(12) United States Patent
Friedman et al.

(10) Patent No.: US 10,940,151 B2
(45) Date of Patent: Mar. 9, 2021

(54) METHODS FOR TREATING RENAL DISEASE

(71) Applicant: Beth Israel Deaconess Medical Center, Inc., Boston, MA (US)

(72) Inventors: David J. Friedman, Boston, MA (US); Martin R. Pollak, Boston, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 16/179,100

(22) Filed: Nov. 2, 2018

(65) Prior Publication Data

US 2019/0117659 A1    Apr. 25, 2019

Related U.S. Application Data

(62) Division of application No. 14/646,055, filed as application No. PCT/US2013/070908 on Nov. 20, 2013, now Pat. No. 10,130,632.

(60) Provisional application No. 61/730,370, filed on Nov. 27, 2012.

(51) Int. Cl.

| *A61K 31/519* | (2006.01) |
| *C07D 513/04* | (2006.01) |
| *C12N 15/113* | (2010.01) |
| *A61K 45/06* | (2006.01) |
| *A61K 31/429* | (2006.01) |
| *A61K 31/4706* | (2006.01) |
| *A61K 31/506* | (2006.01) |
| *A61K 31/517* | (2006.01) |
| *A61K 31/713* | (2006.01) |

(52) U.S. Cl.
CPC .......... *A61K 31/519* (2013.01); *A61K 31/429* (2013.01); *A61K 31/4706* (2013.01); *A61K 31/506* (2013.01); *A61K 31/517* (2013.01); *A61K 31/713* (2013.01); *A61K 45/06* (2013.01); *C07D 513/04* (2013.01); *C12N 15/113* (2013.01); *C12N 2310/14* (2013.01); *C12N 2310/531* (2013.01)

(58) Field of Classification Search
None
See application file for complete search history.

(56) References Cited

U.S. PATENT DOCUMENTS

| 5,591,317 A | 1/1997 | Pitts, Jr. |
| 5,747,470 A | 5/1998 | Becherer et al. |
| 5,783,683 A | 7/1998 | Morrison |
| 5,883,228 A | 3/1999 | Darnell, Jr. et al. |
| 6,413,961 B1 | 7/2002 | Demopulos et al. |
| 6,825,190 B2 | 11/2004 | Moon et al. |
| 6,884,782 B2 | 4/2005 | Huang et al. |
| 7,705,004 B2 | 4/2010 | Song et al. |
| 8,138,339 B2 | 3/2012 | Bauer et al. |
| 8,143,412 B2 | 3/2012 | Priebe et al. |
| 8,258,144 B2 | 9/2012 | Song et al. |
| 9,023,355 B2 | 5/2015 | Friedman et al. |
| 10,130,632 B2 | 11/2018 | Friedman et al. |
| 2003/0166629 A1 | 9/2003 | Choi et al. |
| 2004/0186118 A1* | 9/2004 | Bryant .................... A61P 17/06 514/269 |
| 2005/0009016 A1 | 1/2005 | Moskowitz et al. |
| 2005/0142596 A1 | 6/2005 | Krolewski et al. |
| 2005/0277680 A1 | 12/2005 | Priebe et al. |
| 2006/0106020 A1 | 5/2006 | Rodgers et al. |
| 2006/0183906 A1 | 8/2006 | Rodgers et al. |
| 2007/0135461 A1 | 6/2007 | Rodgers et al. |
| 2007/0149469 A1 | 6/2007 | Korherr |
| 2007/0149506 A1 | 6/2007 | Arvanitis et al. |
| 2008/0188500 A1 | 8/2008 | Arvanitis et al. |
| 2009/0060898 A1 | 3/2009 | Kandimalla et al. |
| 2009/0162333 A1 | 6/2009 | Pays et al. |
| 2010/0098685 A1 | 4/2010 | Zhu et al. |
| 2010/0113416 A1 | 5/2010 | Friedman et al. |
| 2010/0120781 A1 | 5/2010 | Neamati |
| 2012/0022142 A1 | 1/2012 | Jadhav et al. |
| 2012/0129867 A1 | 5/2012 | Bauer et al. |
| 2012/0195902 A1 | 8/2012 | Friedman et al. |

FOREIGN PATENT DOCUMENTS

| WO | WO-2004/012757 A2 | 2/2004 |
| WO | WO-2011/133474 A2 | 10/2011 |
| WO | WO-2012/030912 A1 | 3/2012 |
| WO | WO-2012/162394 A2 | 11/2012 |

OTHER PUBLICATIONS

Schwimmer ("A List of Kidney Diseases" available online at http://www.kidney.nyc/types-of-kidney-disease/—accessed 2017) (Year: 2017).*
Limou et al (Kidney Int 88:754-763, 2015) (Year: 2015).*
Gou et al (Acta Biochim Biophys Sin (Shanghai) 40:426-436, 2008—Abstract only) (Year: 2008).*
Kopp et al (J Ann Soc Nephrol 22:2129-2137, 2011) (Year: 2011).*
Adams et al., "The Bcl-2-regulated apoptosis switch: mechanism and therapeutic potential," available in PMC Sep. 29, 2009, published in final edited form as: Curr Opin Immunol. 19(5):488-96 (2007) (14 pages).
Hu et al., "Human apolipoprotein L1 (ApoL1) in cancer and chronic kidney disease (Review Paper)," available in PMC Apr. 5, 2012, published in final edited form as: FEBS Lett. 586(7):947-55 (2012) (19 pages).
Appel et al., "Intensive blood-pressure control in hypertensive chronic kidney disease," N Engl J Med. 363(10): 918-29 (2010).
Bentley et al., "Variation in APOL1 Contributes to Ancestry-Level Differences in HDLc-Kidney Function Association," Int J Nephrol. 748984 (2012) (10 pages).

(Continued)

*Primary Examiner* — Craig D Ricci
(74) *Attorney, Agent, or Firm* — Clark & Elbing LLP

(57) ABSTRACT

The invention features methods for treating or reducing the likelihood of developing a renal disease by administering to a subject in need thereof an agent that decreases expression of a pathogenic APOL1. The agents of the method target various signaling pathways and decrease the level of the pathogenic APOL1 polypeptide.

13 Claims, 15 Drawing Sheets

Specification includes a Sequence Listing.

(56) References Cited

OTHER PUBLICATIONS

Binshtok et al., "Inhibition of nociceptors by TRPV1-mediated entry of impermeant sodium channel blockers," Nature 449:607-610 (2007).
Breznan et al., "The lipid composition of high-density lipoprotein affects its re-absorption in the kidney by proximal tubule epithelial cells," Biochem J. 379(Pt 2):343-9 (2004).
Clinical Pharmacology Review, Application No. 203214Orig1s000, Center for Drug Evaluation and Research, Oct. 21, 2011 (181 pages).
Cohen et al., "African American living-kidney donors should be screened for APOL1 risk alleles," available in PMC Oct. 26, 2015, published in final edited form as: Transplantation. 92(7):722-5 (2011) (7 pages).
D'Agati et al., "Focal segmental glomerulosclerosis," N Engl J Med. 365(25):2398-411 (2011).
Duchateau et al., "Apolipoprotein L, a new human high density lipoprotein apolipoprotein expressed by the pancreas. Identification, cloning, characterization, and plasma distribution of apolipoprotein L," J Biol Chem. 272(41):25576-82 (1997).
Dummer et al., "APOL1 Kidney Disease Risk Variants: An Evolving Landscape," available in PMC May 1, 2016, published in final edited form as: Semin Nephrol. 35(3):222-36 (2015) (25 pages).
Freedman et al., "The apolipoprotein L1 (APOL1) gene and nondiabetic nephropathy in African Americans," J Am Soc Nephrol. 21(9):1422-6 (2010) (5 pages).
Genovese et al., "Association of trypanolytic ApoL1 variants with kidney disease in African Americans," Science. 329(5993):841-5 (2010).
Gibson et al., "The human serum resistance associated gene is ubiquitous and conserved in *Trypanosoma brucei rhodesiense* throughout East Africa," Infect Genet Evol. 1(3):207-14 (2002).
Guo et al., "How is mRNA expression predictive for protein expression? A correlation study on human circulating monocytes," Acta Biochim Biophys Sin (Shanghai). 40(5):426-36 (2008) (1 page) (Abstract only).
Hartman et al., "Global changes in STAT target selection and transcription regulation upon interferon treatments," Genes Dev. 19(24):2953-68 (2005) (17 pages).
International Preliminary Report on Patentability and Written Opinion for International Application No. PCT/US2013/070908, dated Jun. 11, 2015 (8 pages).
International Search Report and Written Opinion for International Application No. PCT/US13/70908, dated Apr. 23, 2014 (13 pages).
International Search Report and Written Opinion for International Application No. PCT/US12/39145, dated Dec. 7, 2012 (13 pages).
International Search Report for International Application No. PCT/US11/32924, dated Apr. 9, 2012 (6 pages).
Juengst, "What next for human gene therapy? Gene transfer often has multiple and unpredictable effects on cells," BMJ. 326(7404):1410-1 (2003).
Kaufman et al., "Transgenic analysis of a 100-kb human beta-globin cluster-containing DNA fragment propagated as a bacterial artificial chromosome," Blood. 94(9):3178-84 (1999).
Kiberstis, "Letter and reviews from *Science* (1189125)," E-mail to Martin Pollak dated Mar. 16, 2010 (3 pages).
Lecordier et al., "C-terminal mutants of apolipoprotein L-I efficiently kill both *Trypanosoma brucei brucei* and *Trypanosoma brucei rhodesiense*," PLoS Pathog. 5(12):e1000685 (2009) (11 pages).
Li et al., "Distribution and effect of apoL-I genotype on plasma lipid and apolipoprotein levels in Chinese normalipidemic and endogenous hypertriglyceridemic subjects," Clin Chim Acta. 403(1-2):152-5 (2009).
Limou et al., "Sequencing rare and common APOL1 coding variants to determine kidney disease risk," available in PMC Apr. 1, 2016, published in final edited form as: Kidney Int. 88(4):754-63 (2015) (22 pages).

McCleskey, "Neuroscience: a local route to pain relief," Nature. 449(7162):545-6 (2007).
Molina-Portela et al., "Distinct roles of apolipoprotein components within the trypanosome lytic factor complex revealed in a novel transgenic mouse model," J Exp Med. 205(8):1721-8 (2008).
NCBI Blast for Accession No. AA142721.1. Retrieved on Jun. 9, 2015 (2 pages).
NCBI Blast for Accession No. AA143039.1. Retrieved on Jun. 9, 2015 (2 pages).
NCBI Blast for Accession No. AF305224.1. Retrieved on Jun. 9, 2015 (2 pages).
NCBI Blast for Accession No. BC127186.1. Retrieved on Jun. 9, 2015 (3 pages).
NCBI Blast for Accession No. CAQ09089.1. Retrieved on Jun. 9, 2015 (2 pages).
NCBI Blast for Accession No. NC_000022.10. Retrieved on Jun. 9, 2015 (2 pages).
NCBI Blast for Accession No. NM_001136540.1. Retrieved on Jun. 9, 2015 (5 pages).
NCBI Blast for Accession No. NM_145343.2. Retrieved on Jun. 9, 2015 (5 pages).
NCBI Blast for Accession No. NP_003652.2. Retrieved on Jun. 9, 2015 (3 pages).
NCBI Blast for Accession No. Z82215.1. Retrieved on Jun. 9, 2015 (31 pages).
NCBI Reference SNP(refSNP) Cluster Report: rs60910145, <http://www.ncbi.nlm.nih.gov/projects/SNP/snp_ref.cgi?rs=60910145>, retrieved on Dec. 15, 2011 (3 pages).
NCBI Reference SNP(refSNP) Cluster Report: rs73885319, <http://www.ncbi.nlm.nih.gov/projects/SNP/snp_ref.cgi?rs=73885319>, retrieved Dec. 15, 2011 (3 pages).
Office Action in U.S. Appl. No. 13/404,725, dated Aug. 26, 2013 (11 pages).
Page et al., "Polymorphisms in the Apolipoprotein L1 gene and their effects on blood lipid and glucose levels in middle age males," Genes Nutr. 1(2):133-5 (2006).
Page et al., "The human apolipoprotein L gene cluster: identification, classification, and sites of distribution," Genomics 74(1):71-8 (2001).
Paul, "Genes linked to kidney disease," Genetics Abstract, <http://geneticabstracts.blogspot.com/2008/10/genes-linked-to-kidney-disease.html>, retrieved on Aug. 22, 2011 (2 pages).
Schwimmer, "A List of Kidney Diseases," retrieved from <http://www.kidney.nyc/types-of-kidney-disease> (13 pages).
Tzur et al., "Missense mutations in the APOL1 gene are highly associated with end stage kidney disease risk previously attributed to the MYH9 gene," Hum Genet. 128(3):345-50 (2010).
Vanhamme et al., "The trypanosome lytic factor of human serum and the molecular basis of sleeping sickness," Int J Parasitol 34(8):887-98 (2004).
Vanhollebeke et al., "Distinct roles of haptoglobin-related protein and apolipoprotein L-I in trypanolysis by human serum," Proc Natl Acad Sci USA. 104(10):4118-23 (2007).
Vanhollebeke et al., "Human *Trypanosoma evansi* infection linked to a lack of apolipoprotein L-I," N Engl J Med. 355(26):2752-6 (2006).
Wan et al., "Apolipoprotein L1, a novel Bcl-2 homology domain 3-only lipid-binding protein, induces autophagic cell death," J Biol Chem. 283(31): 21540-9 (2008).
Wang et al., "Rapid analysis of gene expression (RAGE) facilitates universal expression profiling," Nucelic Acids Res. 27(23):4609-18 (1999).
Written Opinion of the International Searching Authority for International Application No. PCT/US11/32924, dated Apr. 9, 2012 (8 pages).
Yabu et al., "Rituximab failed to improve nephrotic syndrome in renal transplant patients with recurrent focal segmental glomerulosclerosis," Am J Transplant. 8(1):222-7 (2008).
Kruzel-Davila et al., "APOL1 nephropathy: a population genetics and evolutionary medicine detective story," Semin Nephrol. 37(6):490-507 (2017).
Riella et al., "Testing for high-risk APOL1 alleles in potential living kidney donors," Am J Kidney Dis. 66(3):396-401 (2015).

(56) References Cited

OTHER PUBLICATIONS

Friedman et al., "Apolipoprotein L1 and kidney disease in African Americans," Trends Endocrinol Metab. 27(4):204-215 (2016).
Nichols et al., "Innate immunity pathways regulate the nephropathy gene Apolipoprotein L1," Kidney Int. 87(2):332-42 (2014) (advance online publication) (11 pages).
Clark et al., "Novel cross-talk within the IKK family controls innate immunity," Biochem J 434 (1):93-104, 2011.
Reilly et al., "An inhibitor of the protein kinases TBK1 / IKKε improves obesity-related metabolic dysfunctions," *Nat Med.* 19(3):313-321, 2013.

\* cited by examiner

SEQUENCE LISTING

```
<160> NUMBER OF SEQ ID NOS: 2

<210> SEQ ID NO 1
<211> LENGTH: 1197
<212> TYPE: DNA
<213> ORGANISM: Homo sapiens

<400> SEQUENCE: 1
atggagggag ctgctttgct gagagtctct gtcctctgca tctggatgag tgcactttc      60 cttggtgtgg gagtgagggc agaggaagct ggagcgaggg tgcaacaaaa cgttccaagt    120
gggacagata ctggagatcc tcaaagtaag cccctcggtg actgggctgc tggcaccatg    180
gacccagaga gcagtatctt tattgaggat gccattaagt atttcaagga aaaagtgagc    240
acacagaatc tgctactcct gctgactgat aatgaggcct ggaacggatt cgtggctgct    300
gctgaactgc ccaggaatga ggcagatgag ctccgtaaag ctctggacaa ccttgcaaga    360
caaatgatca tgaaagacaa aaactggcac gataaaggcc agcagtacag aaactggttt    420
ctgaaagagt ttcctcggtt gaaaagtgag cttgaggata acataagaag gctccgtgcc    480
cttgcagatg gggttcagaa ggtccacaaa ggcaccacca tcgccaatgt ggtgtctggc    540
tctctcagca tttcctctgg catcctgacc ctcgtcggca tgggtctggc acccttcaca    600
gagggaggca gccttgtact cttggaacct gggatggagt tgggaatcac agccgctttg    660
accgggatta ccagcagtac catggactac ggaaagaagt ggtggacaca agcccaagcc    720
cacgacctgg tcatcaaaag ccttgacaaa ttgaaggagg tgagggagtt tttgggtgag    780
aacatatcca actttctttc cttagctggc aatacttacc aactcacacg aggcattggg    840
aaggacatcc gtgccctcag acgagccaga gccaatcttc agtcagtacc gcatgcctca    900
gcctcacgcc cccgggtcac tgagccaatc tcagctgaaa gcggtgaaca ggtggagagg    960
gttaatgaac ccagcatcct ggaaatgagc agaggagtca agctcacgga tgtggcccct   1020
gtaagcttct ttcttgtgct ggatgtagtc tacctcgtgt acgaatcaaa gcacttacat   1080 gaggggcaa agtcagagac agctgaggag ctgaagaagg tggctcagga gctggaggag   1140
aagctaaaca ttctcaacaa taattataag attctgcagg cggaccaaga actgtga      1197
```

<210> SEQ ID NO 2
<211> LENGTH: 398
<212> TYPE: PRT
<213> ORGANISM: Homo sapiens

<400> SEQUENCE: 2

```
Met Glu Gly Ala Ala Leu Leu Arg Val Ser Val Leu Cys Ile Trp Met
1               5                   10                  15

Ser Ala Leu Phe Leu Gly Val Val Arg Ala Glu Glu Ala Gly Ala
            20                  25                  30

Arg Val Gln Gln Asn Val Pro Ser Gly Thr Asp Thr Gly Asp Pro Gln
                35                  40                  45

Ser Lys Pro Leu Gly Asp Trp Ala Ala Gly Thr Met Asp Pro Glu Ser
    50                  55                  60

Ser Ile Phe Ile Glu Asp Ala Ile Lys Tyr Phe Lys Glu Lys Val Ser
65                  70                  75                  80

Thr Gln Asn Leu Leu Leu Leu Thr Asp Asn Glu Ala Trp Asn Gly
                85                  90                  95

Phe Val Ala Ala Ala Glu Leu Pro Arg Asn Glu Ala Asp Glu Leu Arg
            100                 105                 110

Lys Ala Leu Asp Asn Leu Ala Arg Gln Met Ile Met Lys Asp Lys Asn
            115                 120                 125

Trp His Asp Lys Gly Gln Gln Tyr Arg Asn Trp Phe Leu Lys Glu Phe
            130                 135                 140

Pro Arg Leu Lys Ser Glu Leu Glu Asp Asn Ile Arg Arg Leu Arg Ala
145                 150                 155                 160

Leu Ala Asp Gly Val Gln Lys Val His Lys Gly Thr Thr Ile Ala Asn
                165                 170                 175

Val Val Ser Gly Ser Leu Ser Ile Ser Ser Gly Ile Leu Thr Leu Val
            180                 185                 190

Gly Met Gly Leu Ala Pro Phe Thr Glu Gly Gly Ser Leu Val Leu Leu
        195                 200                 205

Glu Pro Gly Met Glu Leu Gly Ile Thr Ala Ala Leu Thr Gly Ile Thr
    210                 215                 220

Ser Ser Thr Met Asp Tyr Gly Lys Lys Trp Trp Thr Gln Ala Gln Ala
225                 230                 235                 240

His Asp Leu Val Ile Lys Ser Leu Asp Lys Leu Lys Glu Val Arg Glu
                245                 250                 255

Phe Leu Gly Glu Asn Ile Ser Asn Phe Leu Ser Leu Ala Gly Asn Thr
            260                 265                 270

Tyr Gln Leu Thr Arg Gly Ile Gly Lys Asp Ile Arg Ala Leu Arg Arg
        275                 280                 285

Ala Arg Ala Asn Leu Gln Ser Val Pro His Ala Ser Ala Ser Arg Pro
    290                 295                 300

Arg Val Thr Glu Pro Ile Ser Ala Glu Ser Gly Glu Gln Val Glu Arg
305                 310                 315                 320

Val Asn Glu Pro Ser Ile Leu Glu Met Ser Arg Gly Val Lys Leu Thr
                325                 330                 335

Asp Val Ala Pro Val Ser Phe Phe Leu Val Leu Asp Val Val Tyr Leu
            340                 345                 350

Val Tyr Glu Ser Lys His Leu His Glu Gly Ala Lys Ser Glu Thr Ala
        355                 360                 365

Glu Glu Leu Lys Lys Val Ala Gln Glu Leu Glu Glu Lys Leu Asn Ile
```

|   |   | 370 |   |   |   | 375 |   |   |   | 380 |   |
|---|---|---|---|---|---|---|---|---|---|---|---|
| Leu | Asn | Asn | Asn | Tyr | Lys | Ile | Leu | Gln | Ala | Asp | Gln | Glu | Leu |
| 385 |   |   |   |   | 390 |   |   |   |   | 395 |   |

METHODS FOR TREATING RENAL DISEASE

FIELD OF THE INVENTION

The field of invention is the treatment of renal disease, such as focal segmental glomerulosclerosis (FSGS), end-stage kidney disease (ESKD) or non-diabetic chronic kidney disease, in a subject (e.g., a subject having one or more APOL1 risk alleles and expressing a pathogenic APOL1 polypeptide) by administering an agent that targets specific signaling pathways and thereby decreases APOL1 polypeptide expression.

BACKGROUND OF THE INVENTION

End-stage kidney failure (ESKD) is a growing problem that now affects over half a million individuals in the United States. The cost of caring for patients with ESKD is currently over 40 billion dollars per year. In the U.S., the likelihood that subjects of African descent will develop ESKD is 4 to 5 times higher than for Americans without African ancestry. These facts are reflected in the disparity between the 12-13% of the U.S. population with African descent and the 40% of U.S. dialysis patients who are African-American. The epidemic of renal disease risk factors, such as obesity and metabolic syndrome, suggests that the magnitude of this problem will only increase.

There are no specific therapies for the vast majority of progressive kidney diseases. Some types of chronic renal disease progression can be slowed by blood pressure control with specific agents, but nephrologists cannot accurately predict which patients will respond. Moreover, while successful treatment typically slows progression, it neither prevents disease nor halts disease progression. Recent large trials have shown that African Americans may derive less benefit from drugs used to slow the progression of renal disease (Appel et al., *N.E. J. Med.* 363:918-929, 2010). There are few, if any, common diseases that show such a marked disparity in the United States.

Recently it was determined that that specific genetic variants that alter the protein sequence of APOlipoprotein-L1 (APOL1) are present only in individuals with recent African ancestry and account for a large proportion of this major health disparity. Surprisingly, APOL1 kidney disease variants have a major impact on multiple different types of kidney disease including hypertension-associated end-stage renal disease (H-ESRD), focal segmental glomerulosclerosis (FSGS), and HIV-associated nephropathy (HIVAN). Individuals with these variant APOL1 alleles have a 7-30 fold increased risk for kidney disease. Based on the high frequency of these APOL1 risk alleles, more than 3.5 million African Americans likely have the high risk APOL1 genotype. African Americans without the high risk genotype have little excess risk compared with Americans of European ancestry.

Despite evidence that variants in the APOL1 gene cause renal disease, very little is known about the biology of its product, APOL1, or its role in the kidney. APOL1 has a defined role in resistance to trypanosomes, and the G1 and G2 variants appear to have become common in Africa because they confer protection against the forms of trypanosomes that cause African Sleeping Sickness.

There still exists a need for therapies for kidney diseases in patients with one or more APOL1 risk alleles, which cause great morbidity and mortality with high economic impact in this and other subject populations.

SUMMARY OF THE INVENTION

The invention features methods for treating renal disease in patients with a high-risk APOL1 genotype (e.g., those patients having at least one or more APOL1 risk alleles).

A first aspect of the invention features a method of treating or reducing the likelihood of developing a renal disease by administering to a subject in need thereof an agent (e.g., an agent that targets the Janus Kinase (JAK)/Signal Transduction Activator of Transcription (STAT) pathway, the toll like receptor (TLR) pathway, the NF-κB pathway, the protein kinase R (PKR) pathway, the MAP kinase pathway, and the TANK binding kinase 1 (TBK1)/IκB kinase e (IKKe) pathway) that decreases the level of expression of a pathogenic APOL1 encoded by an APOL1 risk allele.

As used herein, the term "alkyl," "alkenyl" and "alkynyl" include straight-chain, branched-chain and cyclic monovalent substituents, as well as combinations of these, containing only C and H when unsubstituted. Examples include methyl, ethyl, isobutyl, cyclohexyl, cyclopentylethyl, 2-propenyl, 3-butynyl, and the like. The term "cycloalkyl," as used herein, represents a monovalent saturated or unsaturated non-aromatic cyclic alkyl group having between three to nine carbons (e.g., a C3-C9 cycloalkyl), unless otherwise specified, and is exemplified by cyclopropyl, cyclobutyl, cyclopentyl, cyclohexyl, cycloheptyl, bicyclo[2.2.1.]heptyl, and the like. When the cycloalkyl group includes one carbon-carbon double bond, the cycloalkyl group can be referred to as a "cycloalkenyl" group. Exemplary cycloalkenyl groups include cyclopentenyl, cyclohexenyl, and the like Typically, the alkyl, alkenyl and alkynyl groups contain 1-12 carbons (e.g., C1-C12 alkyl) or 2-12 carbons (e.g., C2-C12 alkenyl or C2-C12 alkynyl). In some embodiments, the alkyl groups are C1-C8, C1-C6, C1-C4, C1-C3, or C1-C2 alkyl groups; or C2-C8, C2-C6, C2-C4, or C2-C3 alkenyl or alkynyl groups. Further, any hydrogen atom on one of these groups can be replaced with a substituent as described herein.

The term "alkoxy" represents a chemical substituent of formula —OR, where R is an optionally substituted alkyl group (e.g., C1-C6 alkyl group), unless otherwise specified. In some embodiments, the alkyl group can be substituted, e.g., the alkoxy group can have 1, 2, 3, 4, 5, or 6 substituent groups as defined herein. Similarly, the term "alkaryloxy" represents a chemical substituent of formula —OR, where R is an optionally substituted alkaryl group.

"Aromatic" moiety or "aryl" moiety refers to any monocyclic or fused ring bicyclic system which has the characteristics of aromaticity in terms of electron distribution throughout the ring system and includes a monocyclic or fused bicyclic moiety such as phenyl or naphthyl; "heteroaromatic" or "heteroaryl" also refers to such monocyclic or fused bicyclic ring systems containing one or more heteroatoms selected from O, S, and N. The inclusion of a heteroatom permits inclusion of 5-membered rings to be considered aromatic as well as 6-membered rings. Thus, typical aromatic/heteroaromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, isoxazolyl, benzoxazolyl, benzoisoxazolyl, imidazolyl, and the like. Because tautomers are theoretically possible, phthalimido is also considered aromatic. Typically, the ring systems contain 5-12 ring member atoms or 6-10 ring member atoms.

"Halogen" refers to a halogen atom that is F, Cl, Br, or I, and more particularly is fluorine or chlorine.

An "oxo" group is a substituent having the structure C=O, where there is a double bond between a carbon and an oxygen atom. Similarly, a "thioxo" group is a substituent having the structure C=S, where there is a double bond between a carbon and a sulfur atom.

Typical optional substituents on aromatic or heteroaromatic groups include independently halo (e.g., F, Cl, Br, or I), CN, $NO_2$, $CF_3$, $OCF_3$, COOR', CONR'$_2$, OR', SR, SOR', $SO_2R'$, NR'$_2$, NR'(CO)R',NR'C(O)OR', NR'C(O)NR'$_2$, NR'SO$_2$NR'$_2$, or NR'SO$_2$R', wherein each R' is independently H or an optionally substituted group selected from alkyl, alkenyl, alkynyl, heteroalkyl, heteroalkenyl, heteroalkynyl, heteroaryl, and aryl (all as defined above); or the substituent may be an optionally substituted group selected from alkyl, alkenyl, alkynyl, heteroalkyl, heteroalkenyl, heteroalkynyl, aryl, heteroaryl, O-aryl, O-heteroaryl, and arylalkyl.

Optional substituents on a non-aromatic group (e.g., alkyl, alkenyl, and alkynyl groups), are typically selected from the same list of substituents suitable for aromatic or heteroaromatic groups, except as noted otherwise herein. A non-aromatic group may also include a substituent selected from =O and =NOR' where R' is H or an optionally substituted group selected from alkyl, alkenyl, alkynyl, heteroalkyl, heteroalkenyl, heteralkynyl, heteroaryl, and aryl (all as defined above).

In general, a substituent group (e.g., alkyl, alkenyl, alkynyl, or aryl (including all heteroforms defined above) may itself optionally be substituted by additional substituents. The nature of these substituents is similar to those recited with regard to the substituents on the basic structures above. Thus, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments, and is not included. However, alkyl substituted by aryl, amino, halo and the like would be included. For example, where a group is substituted, the group may be substituted with 1, 2, 3, 4, 5, or 6 substituents. Optional substituents include, but are not limited to: C1-C6 alkyl or heteroaryl, C2-C6 alkenyl or heteroalkenyl, C2-C6 alkynyl or heteroalkynyl, halogen; aryl, heteroaryl, azido(-$N_3$), nitro (—$NO_2$), cyano (—CN), acyloxy(-OC(=O)R'), acyl (—C(=O)R'), alkoxy (—OR'), amido (—NR'C(=O) R" or —C(=O)NRR'), amino (—NRR'), carboxylic acid (—$CO_2$H), carboxylic ester (—$CO_2$R'), carbamoyl (—OC (=O)NR'R" or —NRC(=O)OR'), hydroxy (—OH), isocyano (—NC), sulfonate (—S(=O)$_2$OR), sulfonamide (—S (=O)$_2$NRR' or —NRS(=O)$_2$R'), or sulfonyl (—S(=O)$_2$ R), where each R or R' is selected, independently, from H, C1-C6 alkyl or heteroalkyl, C2-C6 alkenyl or heteroalkenyl, 2C-6C alkynyl or heteroalkynyl, aryl, or heteroaryl. A substituted group may have, for example, 1, 2, 3, 4, 5, 6, 7, 8, or 9 substituents.

By "apheresis," "hemapheresis," or "pheresis" is meant the process of removing a specific component from the blood, plasma, serum, or a fraction thereof, of a subject. Apheresis can be used to remove, separate, or collect one or more specific components of the blood, plasma, serum, or a fraction thereof. In general, apheresis includes the withdrawal of blood from the subject's body, removal of one or more components from the blood, and transfusion of the remaining blood back into the subject's body.

By "apolipoprotein L1" or "APOL1" is meant a gene encoding human apolipoprotein L, 1 (OMIM: 603743; see also SEQ ID NO: 1) or a polypeptide that includes, e.g., amino acids 1-398 of SEQ ID NO: 2. APOL1 is a secreted high density lipoprotein which binds to apolipoprotein A-I. Apolipoprotein A-I is a relatively abundant plasma protein and is the major apoprotein of HDL. Several different transcript variants encoding different isoforms have been found for this gene.

Nucleic acid and protein sequences for human APOL1 are publicly available. For example, GENBANK® Accession No. NC_000022.10 (nucleotides 36649117 . . . 36663577) discloses an exemplary human APOL1 genomic sequence (incorporated by reference as provided by GENBANK® on Apr. 18, 2010). In other examples, GENBANK® Accession Nos. AF305224.1, NM_003661.3, NM_145343.2, NM_001136540.1, z82215, and BC127186.1 disclose exemplary human APOL1 nucleic acid sequences, and GENBANK® Accession Nos. CAQ09089, NP_003652, AAI43039.1, and AA142721.1 disclose exemplary human APOL1 protein sequences, all of which are incorporated by reference as provided by GENBANK® on Apr. 18, 2010.

By "APOL1 risk allele" is meant a form of a gene that is correlated with the development of, or an increased risk of developing, renal disease in a subject (e.g., a human). The risk allele may correspond to a mutation in an APOL1 gene (e.g., a human APOL1 gene) or a mutation in a gene that is involved in the expression of a protein that may interacts with an APOL1 protein or another component of the high density lipoprotein complex. The mutation may result in a modification (e.g., a substitution, deletion, or inversion) in a polypeptide product of a risk allele (e.g., a substitution, deletion, or inversion in an APOL1 polypeptide). Examples of such mutations in an APOL1 polypeptide include, but are not limited to, the G1a, G1b, G1, G2, and G3 mutations described herein and in PCT/US2011/032924, or combinations thereof. The risk of renal disease is elevated in subjects carrying one or more (e.g., two, three, or four) APOL1 risk alleles.

By "common APOL1" is meant an APOL1 polypeptide, or nucleic acid molecule encoding the APOL1 polypeptide, having a sequence that is not correlated to the development of renal disease in a subject (e.g., a human). For example, a common APOL1 is one that includes an amino acid sequence or a nucleic acid sequence set forth above in the definition for "apolipoprotein L1" and "APOL1" (e.g., SEQ ID NOs: 1 and 2), and that does not include one or more mutations that have been correlated with the development of renal disease, such as the G1a, G1 b, G1, G2, and/or G3 mutations described herein and in PCT/US2011/032924.

By "decrease" is meant becoming less or smaller, as in number, amount, size, or intensity. In one example, decreasing the risk of a disease (such as FSGS or hypertensive ESKD) includes a decrease in the likelihood of developing the disease by at least about 20%, for example by at least about 30%, 40%, 50%, 60%, 70%, 80%, or 90%. In another example, decreasing the risk of a disease includes a delay in the development of the disease, for example a delay of at least about six months, such as about one year, such as about two years, about five years, or about ten years.

In one example, decreasing the signs and symptoms of renal disease (e.g., such as FSGS or hypertensive ESKD) includes decreasing the effects of the disease, such as podocyte injury or glomerular scarring by a desired amount, for example by at least 5%, at least 10%, at least 15%, at least 20%, at least 25%, at least 30%, at least 50%, at least 75%, or even at least 90%, as compared to a response in the absence of administration of a therapeutic composition of the invention.

By "isolated" (e.g., as an "isolated" biological component, such as a nucleic acid molecule, protein, antibody, or cell, or as an "isolated" chemical component, such as a compound or other chemical therapeutic agent) is meant that a component has been substantially separated or purified away from other biological (or chemical) components, e.g., as in the cell of an organism in which the component naturally occurs. For example, a component is "isolated" if it is enriched in a composition, relative to other components in the composition, such that it constitutes at least 30%, more preferably at least 50%, or even more preferably at least 75% or more of the composition. A component is "substantially isolated" or "substantially purified" if it is enriched, relative to other components in a composition, such that it constitutes at least 85%, more preferably at least 90%, or even more preferably 95%, 97%, or 99% or more of the composition. Nucleic acids and proteins that have been "isolated" include, e.g., nucleic acid molecules that encode an APOL1 polypeptide or fragment thereof, nucleic acid therapeutics of the invention, such an antisense mRNA molecules, protein antagonists of APOL1 gene expression, such as those described herein, and antagonist antibodies (e.g., antibodies that target one or more components of pathways (e.g., those described herein) that are involved in APOL1 gene expression), each of which may be purified by standard purification methods. The term also embraces nucleic acid molecules and proteins prepared by recombinant expression in a host cell as well as chemically synthesized nucleic acid molecules, peptides, and polypeptides (e.g., one or more of the nucleic acid molecules, proteins, and antibodies of the invention).

By "pathogenic APOL1" is meant an APOL1 polypeptide, or nucleic acid molecule encoding the APOL1 polypeptide, having a sequence that is correlated to the development of renal disease in a subject (e.g., a human). For example, a pathogenic APOL1 is one that includes an amino acid sequence or a nucleic acid sequence set forth above in the definition for "apolipoprotein L1" and "APOL1" (e.g., SEQ ID NOs: 1 and 2), but that also includes one or more mutations that have been correlated with the development of renal disease, such as the G1a, G1 b, G1, G2, and/or G3 mutations described herein and in PCT/US2011/032924.

By "renal disease" is meant a disorder that specifically leads to damage of the kidneys. Renal diseases include but are not limited to FSGS, hypertensive ESKD, nephropathy secondary to systemic lupus erythematosus, diabetic nephropathy, hypertensive nephropathy, IgA nephropathy, nephritis, HIV-associated nephropathy, non-diabetic chronic kidney disease, and xanthine oxidase deficiency.

Renal disease can be chronic or acute. Chronic renal disease, or the type detected with the assays disclosed herein can progress from stage 1 to stage 2, stage 3, stage 4 or stage 5. The stages of chronic renal disease are:

Stage 1: Slightly diminished kidney function; Kidney damage with normal or increased GFR (>90 mL/min/1.73 m2). Kidney damage is defined as pathologic abnormalities or markers of damage, including abnormalities in blood or urine test or imaging studies.

Stage 2: Mild reduction in GFR (60-89 mL/min/1.73 m2) with kidney damage. Kidney damage is defined as pathologic abnormalities or markers of damage, including abnormalities in blood or urine test or imaging studies.

Stage 3: Moderate reduction in GFR (30-59 mL/min/1.73 m2)

Stage 4: Severe reduction in GFR (15-29 mL/min/1.73 m2)

Stage 5: Established kidney failure (GFR <15 mL/min/1.73 m2, or permanent renal replacement therapy (RRT).

The term "pharmaceutically acceptable salt," as used herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, S. M. Berge et al. describe pharmaceutically acceptable salts in detail in *J. Pharm. Sci.* 66:1-19, 1977. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

By "specifically binds" is meant the preferential association of a binding moiety (e.g., an antibody, antibody fragment, or antagonist of an APOL1 gene expression pathway component) to a target molecule (e.g., a component of a pathway involved in expression of a pathogenic APOL1 protein, such as those described herein) in a sample (e.g., a biological sample) or in vivo or ex vivo. It is recognized that a certain degree of non-specific interaction may occur between a binding moiety and a non-target molecule. Nevertheless, specific binding may be distinguished as mediated through specific recognition of the target molecule. Specific binding results in a stronger association between the binding moiety (e.g., an antibody or fragment thereof) and, e.g., an antigen (e.g., a component of a pathway involved in expression of a pathogenic APOL1 protein) than between the binding moiety and, e.g., a non-target molecule. For example, the antibody may have, e.g., at least 10-fold greater affinity (e.g., 10, $10^2$-, $10^3$-, $10^4$-, $10^9$-, $10^6$-, $10^7$-, $10^8$-, $10^9$-, or $10^{10}$-fold greater affinity) to the component of a pathway involved in expression of a pathogenic APOL1 protein than to non-target protein.

By "subject" or "patient" is meant a living multi-cellular vertebrate organism, a category that includes human and non-human mammals (such as laboratory or veterinary subjects).

By "therapeutically effective amount" is meant an amount of a therapeutic agent (e.g., an agent, such as an antagonist, that targets a component of a pathway involved in expression of a pathogenic APOL1 protein) that alone, or together with one or more additional (optional) therapeutic agents, induces a desired response. In one example, the desired response is decreasing the risk of developing FSGS or decreasing the signs and symptoms of FSGS. For example, a therapeutically effective amount of an antagonist of a component of a pathway involved in expression of a pathogenic APOL1 can be used to treat, prevent, or ameliorate renal disease or reduce one or more symptoms associated with renal disease.

Ideally, a therapeutically effective amount provides a therapeutic effect without causing a substantial cytotoxic effect in the subject. The preparations disclosed herein are administered in therapeutically effective amounts. In general, a therapeutically effective amount of a composition administered to a subject (e.g., a human subject) will vary depending upon a number of factors associated with that subject, for example the overall health of the subject, the condition to be treated, or the severity of the condition. A therapeutically effective amount of a composition can be determined by varying the dosage of the product and measuring the resulting therapeutic response. The therapeutically effective amount can be dependent on the source applied, the subject being treated, the severity and type of the condition being treated, and the manner of administration.

In one example, a desired response is to prevent the development of renal disease (e.g., FSGS). In another example, a desired response is to delay the development or progression of renal disease (e.g., FSGS), for example, by at least about three months, at least about six months, at least about one year, at least about two years, at least about five years, or at least about ten years. In another example, a desired response is to decrease the signs and symptoms of renal disease (e.g., FSGS), such as inflammation and/or scarring of the tissues of the kidney, and/or neurological symptoms in the limbs or associated with speaking.

By "treatment," with respect to renal disease, is meant (1) inhibiting development of symptoms of the disease, e.g., causing the clinical symptoms of the disease not to develop in an animal (e.g., a human) that may have or be predisposed to develop the disease but does not yet experience or display symptoms of the disease, (2) inhibiting the disease, e.g., arresting the development of the disease or one or more of its clinical symptoms, or (3) relieving or ameliorating the disease, e.g., causing regression of the disease or one or more of its clinical symptoms. For example, treatment can refer to relieving one or more symptoms associated with renal disease. Treatment of a disease does not require a total absence of disease. For example, a decrease of at least 25% or at least 50% of one or more of the symptoms or undesired consequences of the disease can be sufficient.

DETAILED DESCRIPTION

Figure 1:
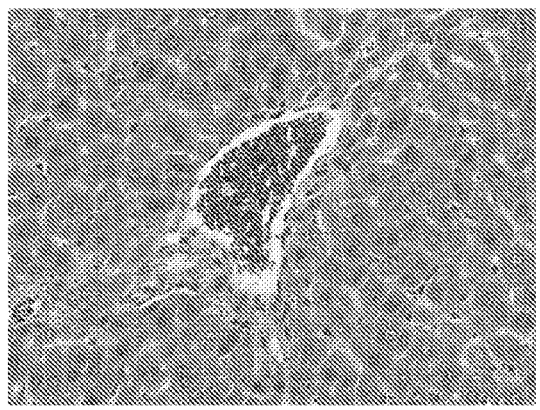
FIG. 1 is a set of images showing cross-section of mice liver injected with WT APOL1 cDNA (left image) or the G1 risk variant APOL1 cDNA (right). The risk variant causes severe and widespread liver injury.
Figure 1:
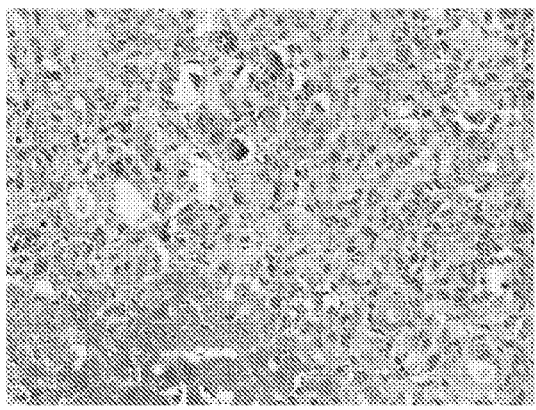

We have discovered that blocking specific signaling pathways causes a decrease in the pathogenic expression of APOL1 polypeptide, thus providing a method of treatment of renal disease in subjects having a APOL1 risk variant allele. The invention features agents that target specific signaling pathways, e.g., one or more of the JAK/STAT pathway, the TLP pathway, the NF-κB pathway, PKR pathway, the MAP kinase pathway, and the TBK1/IKKe pathway.

About 4 to 5-fold increased risk of non-diabetic end-stage renal disease among African-Americans is caused primarily by mutations in the gene encoding Apolipoprotein L1 (APOL1), a component of the densest, HDL3 fraction of high-density lipoprotein. These mutations result in amino acid deletions, substitutions, and inversions (see, e.g., PCT/US2011/032924, which is incorporated herein by reference). APOL1 variants, commonly found among the subjects of African descent (e.g., African-Americans and subjects from some regions of Africa), are among the most powerful genetic risk factors for any disease yet described in terms of frequency and effect size. APOL1 variants can be identified by the presence of single nucleotide polymorphisms (SNPs) in the APOL1 gene (e.g., a SNP within the C-terminal exon of an APOL1 gene, such as the G1a, G1 b, and/or G1 risk alleles), a deletion in the APOL1 gene (e.g., the G2 risk allele), and/or at least one inversion in an APOL1 gene (e.g., an inversion in a 5' region of an APOL1 gene, e.g., an inversion in which the 5' region of an APOL1 gene is replaced with a 5' region of an APOL4 gene, such as the G3 risk allele). The first allele, G1, codes for two amino acid substitutions (S342G and I384M) near the C-terminus that nearly always occur together (the presence of the first mutation alone, S342G is referred to as the G1a risk allele, while the presence of the second mutation, I384M, is referred to as the G1b risk allele). The second allele, G2, is a 6 base pair deletion leading to a loss of amino acid residues 388 and 389 in APOL1. G1 and G2 are mutually exclusive, meaning they have not been observed to occur on the same chromosome. Inheritance of two risk alleles (one from each parent) leads to markedly increased risk of renal disease, whereas one risk allele causes only a very small increase in risk. G1 and G2 forms of APOL1 were both shown to protect against the trypanosomes that cause the deadliest form of African Sleeping Sickness, likely explaining their high frequency in Africans and African Americans. With allele frequencies in African Americans of 23% and 15%, respectively, G1 and G2 are among the most powerful common risk variants discovered to date. Because G1 and G2 are so common in Africans, African Americans, and others of recent African ancestry, we refer to the most common non-risk (wild-type) allele as G0. The major APOL1 haplotypes are shown in Table 1 below.

TABLE

| Combinations of amino acid variants comprising the major APOL1 haplotypes | | | | | | | | | |
|---|---|---|---|---|---|---|---|---|---|
| | E150K | N176S | M228I | K255R | G270D | D337N | S342G | I384M | Del388-9 |
| G0 ("WT") | E | N | M | R | G | D | S | I | |
| G1 | E | N | I | K | G | D | G | M | |
| G1a | E | N | I | K | G | D | G | I | |
| G1b | E | N | I | K | G | D | S | M | |
| G2 | E | N | I | K | G | D | S | I | deletion |
| APOL1a | K | N | I | K | G | D | S | I | |
| APOL1b | E | N | I | K | G | N | S | I | |
| APOL1c | E | S | I | K | G | N | S | I | |
| APOL1d | E | N | I | K | D | N | S | I | |
| APOL1e | E | N | I | K | G | D | S | I | |

Expression of these risk variants (risk alleles) accounts for most of the increased risk of renal disease among African-Americans for several non-diabetic kidney diseases, including hypertension-associated kidney disease, focal segmental glomerulosclerosis, and HIV nephropathy (where the increase in risk is nearly 100 fold). A selective advantage of these polymorphisms also accounts for their high frequency. Individuals having these alleles experience increased protection against African sleeping sickness caused by the parasite *Trypanosoma brucei rhodesiense*. Whereas protection against sleeping sickness is a dominant trait, increased risk of renal disease behaves largely as a recessive trait. The compositions and methods described herein can be used to target these variant APOL1 proteins and/or their biological effects. Such an approach can be used to protect patients with one or more susceptible genotypes against the associated increased risk of renal disease, e.g., end-stage renal disease, as well as other patients having or likely to develop renal disease.

APOL1 has evolved recently under high selective pressure and is found only in humans and a few other primate species. APOL1 has been extensively studied as a component of trypanolytic factor 1 (TLF-I), but almost nothing else is known about APOL1 biology in higher primates. The few published papers document the presence of APOL1 in HDL, but its function in this complex is unknown.

APOL1 variants increase risk of renal disease from multiple etiologies. Expression of two or more risk-associated APOL1 variants increases disease risk between 10- and 100-fold. For example, the risk increase is approximately 7 to 10-fold in H-ESRD, 10-17-fold in FSGS, and 30-fold for HIV. Since the same variants have such profound effects on distinct types of kidney disease, similar pathogenic mechanisms may underlie the enhanced risk for all these entities, if not the disease mechanisms themselves. We believe this increase in risk represents one of the largest ever attributed to common variants. In this context we suggest that APOL1-related kidney disease might be better characterized as a Mendelian disease with modifiers, rather than a common, complex disease.

Nephrologists have little to offer to their patients to slow the progression of diagnosed renal diseases, such as FSGS and ESKD. Current treatments include, e.g., angiotensin-converting enzyme inhibitors (ACEi) and angiotensin II receptor blockers (ARBs), but these treatments are non-specific and only moderately effective. Very few patients respond to steroids, and many of those only transiently.

The APOL1 protein product is a secreted lipoprotein with homology to Bcl-2 family members (Duchateau et al., *J. Biol. Chem.* 272:25576-25582, 1997; and Wan et al., *J. Biol. Chem.* 283:21540-21549, 2008). It circulates as part of HDL3 complexes, the densest HDL fraction, and is expressed in multiple tissue types. It has putative roles in autophagy and apoptosis, and plays an important role in the innate immune system as the human trypanolytic factor that protects humans and some other primates from parasites of the trypanosomida family. The renal risk variants prevent the C-terminus of APOL1 from binding to the trypanosome virulence factor SRA. Evolution of the SRA factor to bind the leucine zipper of APOL1 suggests the existence of an endogenous binding partner for APOL1 that may be critical in governing its function.

APOL1's BH3-only domain strongly suggests a role in apoptosis. BH3-only proteins are pro-apoptotic because they antagonize anti-apoptotic Bcl2 family members with BH3-binding grooves such as Bcl2 itself (Adams et al., *Curr. Opin. Immunol.* 19:488-496, 2007). In our studies, we observed frequent cell death in oocytes injected with APOL1. However, when we co-injected Bcl-XL (a Bcl-2-like anti-apoptotic protein) together with APOL1, oocyte death was essentially eliminated. This finding suggests that APOL1 causes apoptotic cell death via its BH3 domain.

We have discovered that agents (e.g., agents that target specific signaling pathways such as the the JAK/STAT pathway, the TLP pathway, the NF-κB pathway, PKR pathway, the MAP kinase pathway, and the TBK1/IKKe pathway) that decrease the deleterious effects of pathogenic APOL1 high risk variants provide a beneficial therapy for patients having or that will progress to end-stage renal disease, as well as those patients that will likely require renal replacement therapy.

Susceptibility to kidney disease associated with the high-risk variants of APOL1 behaves like a recessive trait (Genovese et al., *Science* 329:841-845, 2010). For example, we observed that a human (age 51) with homozygous null APOL1 mutations that was identified after infection with the opportunistic pathogen *Trypanosoma evansii* displayed no evidence of either renal dysfunction or additional immune dysfunction. This suggests a gain-of-function phenotype of APOL1 renal risk variants despite recessive inheritance. In addition, heterozygotes appear not to develop renal disease, suggesting that the wild-type protein variant protects against coexpressed renal risk variants in APOL1 heterozygotes. Furthermore, the presence of two high-risk APOL1 alleles confers approximately 10-fold increased risk of FSGS and (in the context of HIV infection) approximately 100-fold increased risk of HIV nephropathy. Also, HDL3, which contains APOL1, appears to be filtered by the glomerulus (Breznan et al., *Biochem. J.* 379:343-349, 2004), and APOL1 protein is immunodetected at high levels in proximal tubular epithelial cells, likely reflecting endocytic uptake of filtered HDL3, as well as in the glomerulus and renal vasculature. Among the six human APOL gene products, APOL1 is the only secreted protein.

Circulating APOL1 acts on trypanosomes via trypanosome receptor uptake and subsequent trafficking through the endosomal pathway to the lysosome. The high risk variants of APOL1 are similarly endocytosed from glomerular filtrate and the interstitial fluid by the kidney, and these processes appear to be required for accelerated progression of renal disease in affected individuals. In view of these observations, the invention provides methods for targeting various signaling pathways to decrease the expression level of the pathogenic APOL1 variants in patients having or likely to develop renal disease, which thereby treats or reduces the symptoms or likelihood of developing renal disease in patients at risk.

METHODS OF THE INVENTION

The methods of the invention include the administration of one or more agents that target one or more signaling pathways (e.g., one or more components of the JAK/STAT pathway, the TLP pathway, the NF-κB pathway, PKR pathway, the MAP kinase pathway, and the TBK1/IKKe pathway) in cells of a patient, thereby decreasing the expression levels of a pathogenic APOL1 polypeptide, which is encoded by an APOL1 risk allele in the patient. The agents of the invention can be administered to treat or prevent renal disease (e.g., FSGS, ESKD or non-diabetic chronic kidney disease) or to ameliorate or reduce one or more symptoms of renal disease, in patients in need thereof (e.g., patients having one or more APOL1 risk alleles). The invention features methods of treating a subject (e.g., a human subject) having or at risk of developing a renal disease.

One or more of the agents of the invention can also be administered to a subject in need of kidney transplantation (e.g., prior to or after transplantation). In a preferred embodiment, the subject is one that has been found to have at least one APOL1 gene risk allele (e.g., a G1a, G1b, G1, G2, and/or G3 mutation). It is known that individuals of African ancestry, including those individuals of Hispanic ancestry and, in particular, African-Americans, have an elevated risk for carrying one or two copies of at least one risk allele of the APOL1 gene, which increases their risk of developing idiopathic kidney disease. Thus, in one embodiment, a kidney recipient can be genotyped to determine if the recipient carries one, two, or more copies of at least one of the disclosed risk alleles of the APOL1 gene and can be treated prior to or after kidney transplantation with one or more of the agents of the invention. Additionally, a kidney selected for transplantation can be treated with one or more of the compositions of the invention prior to transplantation of the kidney into the recipient.

The agents of the invention can target any one or more components of the JAK/STAT pathway, the TLP pathway, the NF-κB pathway, PKR pathway, the MAP kinase pathway, and the TBK1/IKKe pathway. To monitor the efficacy of the treatment, methods for assaying levels of APOL1 expression after administration of an agent of the invention (e.g., an agent targeting any one or more components of the JAK/STAT pathway, the TLP pathway, the NF-κB pathway, PKR pathway, the MAP kinase pathway, and the TBK1/IKKe pathway) can be used. These methods can include, e.g., western blotting, immunoprecipitation, ELISA, and q-RT-PCR.

Agents that Target the Janus Kinase (JAK)/Signal Transduction Transcriptional Activation (STAT) Pathway The methods of the invention feature the administration of agents (e.g., antagonists) that target one or more components of the JAK/STAT pathway, thereby decreasing the levels of APOL1 polypeptide expression (e.g., a pathogenic APOL1) in a cell. Administration of the agent(s) treats, prevents, reduces, ameliorates, or alleviates one or more symptoms of a renal disease (e.g., FSGS, ESKD, or non-diabetic chronic kidney disease). The agent(s) target can target any one or more of JAK1, JAK2, JAK3, and TYK2. For example, these agents can be antagonists of JAKs that decrease pathogenic APOL1 polypeptide expression caused by inflammatory factors. The JAK antagonists can be any one or more of lestaurtinib, CP-690550 (tofacitinib), ruxolitinib, SB1518 (pacritinib), CYT387, LY3009104, INCB28050 (baricitinib), TG101348, SD1008, cucrbitacin, GO6976, WHI-P154, and AG490.

JAK inhibitors that may be used in the present invention are described in U.S. patent application publication Nos.: 20100113416, 20070135461, 20060106020, 20060183906, 20070149506, 20080188500, and in U.S. Pat. Nos. 7,705,004; 8,258,144; and 8,138,339; and 6,825,190 (each of which is incorporated herein by reference).

The agents can target specific JAKs, or may target more than one JAK simultaneously. For example, lestaurtinib targets JAK2, CP-690550 (tofacitinib) targets JAK3, ruxolitinib targets JAK1 and JAK2, SB1518 (pacritinib) targets JAK2, CYT387 targets JAK2, LY3009104 and INCB28050 (baricitinib) targets JAK1 and JAK2, TG101348 targets JAK2, SD1008 targets JAK2, cucrbitacin targets JAK2, WHI-P154 targets JAK3, and AG490 targets JAK2.

The agent can also target STAT1, STAT2, STAT3, STAT4, STAT5, and/or STATE. STAT inhibitors that may be used in the methods of the invention are described in U.S. Pat. Nos. 6,884,782 and 8,143,412 (each of which is incorporated herein by reference).

The agents can target specific STATs, or may target more than one STAT simultaneously and can be any one or more of WP1066 (targets STAT3); WP1064 (targets STAT3 and STAT5); STA21; STAT3 Inhibitor V, Stattic; STAT3 Inhibitor VI, S3I-201; STAT3 Inhibitor VII; cucurbitacin (targets STAT3); SD1008 (targets STAT3) and STAT3 InhibitorVIII, 5, 15-DPP.

In some embodiments of the above aspects, the agents may also target one or more JAK and/or STAT targets simultaneously.

Agents that Target the Toll-Like Receptor (TLR) Pathway

The methods of the invention also feature the administration of one or more agents (e.g., antagonists) that target one or more components of the TLR pathway, thereby decreasing the levels of APOL1 polypeptide expression (e.g., a pathogenic APOL1) in a cell. Administration of the agent(s) treats, prevents, reduces, ameliorates, or alleviates one or more symptoms of a renal disease (e.g., FSGS, ESKD, or non-diabetic chronic kidney disease). These agents target can target any one or more of TLR1, TLR2, TLR3, TLR4, TLR5, TLR6, TLR7, TLR8, TLR9, TLR10, TLR11, TLR12, and TLR13. For example, these agents can be antagonists of the TLRs that decrease pathogenic APOL1 polypeptide expression caused by inflammatory factors. The TLR antagonists can be any one or more of eritoran, naloxone, naltrexone, LPS-RS, ibudilast, propentofulline, amitriptyline, ketotifen, cyclobenzaprine, mianserin, imipramine, RSCL-0518, RSCL-0519, RSCL-0575, RSCL-0521, RSCL-0520, RSCL-0638, and RSCL-0522, eritoran, chloroquine, and an oligonucleotide-based antagonist. Oligonucleotide-based TLR antagonists include one or more of those described in e.g., U.S. Patent Application Publication No. 20090060898 (incorporated herein by reference). Additional TLR antagonists that may be used in the methods of the invention are described in U.S. Patent Application Publication No. 20100098685 (incorporated herein by reference).

Agents that Target the NF-κB Pathway

The methods of the invention feature the administration of one or more agents (e.g., an antagonist) that target the NF-κB pathway, thereby decreasing the levels of APOL1 polypeptide expression (e.g., a pathogenic APOL1) in a cell. Administration of the agent(s) treats, prevents, reduces, ameliorates, or alleviates one or more symptoms of a renal disease (e.g., FSGS, ESKD, or non-diabetic chronic kidney disease). For example, these agents can be antagonists of NF-κB that decrease pathogenic APOL1 polypeptide expression caused by inflammatory factors. The NF-κB antagonists can be any one or more of Disulfiram, olmesartan, dithiocarbamates, 2-(1,8-naphthyridin-2-yl)-Phenol, 5-Aminosalicylic acid, BAY 11-7082, BAY 11-7085, CAPE (Caffeic Acid Phenethylester), Diethylmaleate, IKK-2 Inhibitor IV, IMD0354, lactacystin, MG-132 [Z-Leu-Leu-Leu-CHO], NFκB Activation Inhibitor III, NF-κB Activation Inhibitor II, JSH-23, parthenolide, phenylarsine oxide, PPM-18, pyrrolidinedithiocarbamic acid ammonium salt, QNZ, RO 106-9920, rocaglamide, rocaglamide AL, rocaglamide C, rocaglamide I, rocaglamide J, rocaglaol, (R)-MF-132, sodium salicylate, triptolide (PG490), 6A4Q, capsaicin, andrographolide, aurothiomalate, (5Z)-7-oxozeanol, evodiamine, helenalin, gliotoxin, hypoestoxide, NF-κB inhibitor, NF-κB inhibitor V 5HPP-33, NF-κB inhibitor VI BOT-64, NF-κB inhibitor VII CID-2858522, NF-κB inhibitor VIII A-UBI, SN50, SN50M, NF-κB inhibitor VIII EVP4593, nodinitib, oridonin, PPM-18, parthenolide, sulfasalazine, ursolic acid, TIRAP inhibitor peptide, and wedelolactone. Additional NF-κB inhibitors that may be used in the methods of the invention are described e.g., in U.S. Pat. No. 6,410,516 (incorporated herein by reference).

Agents that Target the MAP Kinase Pathway

The methods of the invention feature the administration of one or more agents (e.g., antagonists) that target one or more components of the MAP kinase pathway, thereby decreasing the levels of APOL1 polypeptide expression (e.g., a pathogenic APOL1) in a cell. Administration of the agent(s) treats, prevents, reduces, ameliorates, or alleviates one or more symptoms of a renal disease (e.g., FSGS, ESKD, or non-diabetic chronic kidney disease). For example, these agents can be antagonists of the p38 MAP kinase that decrease pathogenic APOL1 polypeptide expression caused by inflammatory factors. The MAP kinase antagonists can be any one or more of CAY10571, JX-401, MK2a inhibitor, p38 MAP kinase inhibitor, p38 MAP kinase inhibitor III, p38 MAP kinase inhibitor IV, CGH 2466, p38 MAP kinase inhibitor V, PD169316, SB202190, SB203580, SB239063, SB220025, SD-169, RWJ 67657, Antibiotic LL Z1640-2, SCIO 469 hydrochloride, Tie2 kinase inhibitor, VX 475, p38 MAP kinase inhibitor IX, SX 011, TAK 715, VX 702, SB 202190 hydrochloride, ZM 336372, SKF 86002, pamapimod, PF-797804, SB203580, SP600125, SB202190, and SB239906, and doramapimod. Additional MAP kinase antagonists that may be used in the methods of the invention are described, for example, in U.S. Patent Application Publication No. 20120129867 (incorporated herein by reference).

Agents that Target the Protein Kinase R (PKR) Pathway

The methods of the invention feature the administration of one or more agents (e.g., antagonists) that target one or more components of the PKR pathway, thereby decreasing the levels of APOL1 polypeptide expression (e.g., a pathogenic APOL1) in a cell. Administration of the agent(s) treats, prevents, reduces, ameliorates, or alleviates one or more symptoms of a renal disease (e.g., FSGS, ESKD, or non-diabetic chronic kidney disease). For example, these agents can be antagonists of the protein kinase R (PKR) that decrease pathogenic APOL1 polypeptide expression caused by inflammatory factors. The PKR antagonist can have a general structure according to the following formula (I),

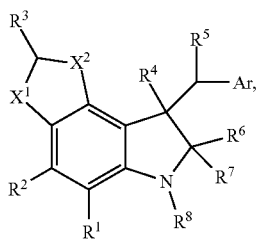

(I)

or a stereoisomer thereof, or a pharmaceutically acceptable salt thereof, wherein each of $R^1$ and $R^2$ is, independently, selected from H, optionally substituted C1-C6 alkyl, optionally substituted C1-C6 alkoxy, halogen, or CN; each of $X^1$ and $X^2$ is, independently, selected from O, S, $NR^X$, or $C(R^X)_2$, where each $R^X$ is, independently, H or optionally substituted C1-C6 alkyl, or one $R^X$ can combine with $R^3$ to form a double bond; $R^3$ is H, optionally substituted C1-C6 alkyl, or halogen, or $R^3$ combines with one $R^X$ to form a double bond; $R^4$ is H, or $R^4$ combines with $R^5$ to form a double bond, or $R^4$ combines with $R^5$ to form a double bond; $R^5$ is H or optionally substituted C1-C6 alkyl, or $R^5$ combines with $R^4$ to form a double bond; each of $R^6$ and $R^7$ is, independently, H or optionally substituted C1-C6 alkyl, or $R^6$ combines with $R^4$ to form a double bond, or $R^6$ and $R^7$ combine to form an oxo (=O) or a thioxo (=S) group; $R^8$ is H or optionally substituted C1-C6 alkyl; and Ar is an optionally substituted phenyl or an optionally substituted five- or six-membered heteroaryl.

The antagonist can have the structure according to formula (I-A),

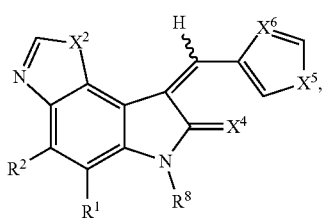

(I-A)

or a stereoisomer thereof, or a pharmaceutically acceptable salt thereof, wherein $X^4$ is O or S; $X^5$ is O, S, or $NR^X$; and $X^6$ is N or CH.

The PKR antagonist can also have the structure

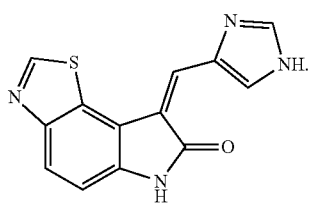 [SMILES: O=C1Nc2ccc3ncsc3c2/C1=C/c1c[nH]cn1]

Alternatively, the PKR antagonist can be 2-aminopurine or P58IPK.

Agents that Target the TANK-Binding Kinase (TBK) 1/IκB Kinase e (IKKe) Pathway

The methods of the invention feature the administration of one or more agents (e.g., antagonists) that target one or more components of the TBK1/IKKe pathway, thereby decreasing the levels of APOL1 polypeptide expression (e.g., a pathogenic APOL1) in a cell. Administration of the agent(s) treats, prevents, reduces, ameliorates, or alleviates one or more symptoms of a renal disease (e.g., FSGS, ESKD, or non-diabetic chronic kidney disease). For example, these agents can be antagonists of the TBK1/IKKe pathway that decrease pathogenic APOL1 polypeptide expression caused by inflammatory factors. The TBK1/IKKe antagonists can be any one or more of Bx795, auranofinc, PS-1145 dihydrochloride, wedelolactone, IKK inhibitor X, butein, and IKK16, The TBK1/IKKe antagonist can also be any one or more of binding proteins or binding peptides directed against TBK-1, in particular against the active site of TBK-1, and nucleic acids directed against the TBK-1 gene. Preferably, the inhibitor binds to the ATP-binding site of the kinase domain of TBK-1. The TBK1/IKKe antagonists can be selected from the group consisting of antisense oligonucleotides, antisense RNA, siRNA, and low molecular weight molecules (LMWs), which are not proteins, peptides antibodies or nucleic acids, and which exhibit a molecular weight of less than 5000 Da, preferably less than 2000 Da, more preferably less than 2000 Da, most preferably less than 500 Da as described in U.S. Patent Application Publication No.: 20070149469.

Therapeutic RNA Interference Agents of the Invention that Target Expression of APOL1

The present invention also features the administration of one or more therapeutic ribonucleic acid interference agents (RNAi) that can be used to decrease the levels of APOL1 polypeptide expression (e.g., a pathogenic APOL1) in a cell for the treatment of disease (e.g., a renal disease). For example, the agents may be RNAi agents that target one or more components of the JAK/STAT pathway, the TLP pathway, the NF-κB pathway, PKR pathway, the MAP kinase pathway, and/or the TBK1/IKKe pathway, thereby decreasing the levels of APOL1 polypeptide expression (e.g., a pathogenic APOL1) in a cell. Administration of one or more of these RNAi agents treats, prevents, reduces, ameliorates, or alleviates one or more symptoms of a renal disease (e.g., FSGS, ESKD, or non-diabetic chronic kidney disease).

Such therapeutic RNAi agents include, e.g., antisense nucleobase oligomers, microRNAs, dsRNA, or small interfering RNAs that downregulate expression of APOL1 mRNA directly.

The RNAi agents can decrease pathogenic APOL1 polypeptide expression by downregulating the expression of one or more genes selected form the group consisting of JAK1, JAK2, JAK3, STAT1, STAT2, STAT3, STAT4, STAT5A, STATE, NEMO, REL-1, TLR3, TICAM1, TBK1, IRF1, IRF2, IRF3, and IRF9.

Methods for assaying levels of APOL1 protein expression after RNA interference are also well known in the art and include, e.g., Western blotting, immunoprecipitation, and ELISA.

RNA Interference Agents

While the first described RNAi molecules were RNA: RNA hybrids comprising both an RNA sense and an RNA antisense strand, it has now been demonstrated that DNA sense:RNA antisense hybrids, RNA sense:DNA antisense hybrids, and DNA:DNA hybrids are capable of mediating RNAi (Lam berton et al., *Molec. Biotechnol.* 24:111-119, 2003). Thus, the invention includes the use of RNAi molecules comprising any of these different types of double-stranded molecules, which can be used to reduce expression of a pathogenic APOL1. In addition, it is understood that RNAi molecules may be used and introduced to cells in a variety of forms. Accordingly, as used herein, RNAi molecules encompasses any and all molecules capable of inducing an RNAi response in cells, including, but not limited to, double-stranded polynucleotides comprising two separate strands, i.e. a sense strand and an antisense strand, e.g., small interfering RNA (siRNA); polynucleotides comprising a hairpin loop of complementary sequences, which forms a double-stranded region, e.g., shRNAi molecules, and expression vectors that express one or more polynucleotides capable of forming a double-stranded polynucleotide alone or in combination with another polynucleotide.

RNA interference (RNAi) may be used to specifically inhibit expression of target polynucleotides (e.g., one or more genes selected form the group consisting of JAK1, JAK2, JAK3, STAT1, STAT2, STAT3, STAT4, STAT5A, STATE, NEMO, REL-1, TLR3, TICAM1, TBK1, IRF1, IRF2, IRF3, and IRF9). Double-stranded RNA-mediated suppression of gene and nucleic acid expression may be accomplished according to the invention by introducing dsRNA, siRNA or shRNA into cells or organisms. SiRNA may be double-stranded RNA, or a hybrid molecule comprising both RNA and DNA, e.g., one RNA strand and one DNA strand. It has been demonstrated that the direct introduction of siRNAs to a cell can trigger RNAi in mammalian cells (Elshabir et al., Nature 411:494-498, 2001). Furthermore, suppression in mammalian cells occurred at the RNA level and was specific for the targeted genes, with a strong correlation between RNA and protein suppression (Caplen et al., Proc. Natl. Acad. Sci. USA 98:9746-9747, 2001). In addition, it was shown that a wide variety of cell lines, including HeLa S3, COS7, 293, NIH/3T3, A549, HT-29, CHO-KI and MCF-7 cells, are susceptible to some level of siRNA silencing (Brown et al., TechNotes 9(1):1-7, 2002).

Exemplary RNAi agents include siRNA, shRNA, dsRNA, and miRNA agents. In certain embodiments, the RNAi agent is a small interfering RNA (siRNA). These are short (usually 21 nt) and are usually double-stranded RNA (dsRNA). siRNA molecules may have, for example, 1 or 2 nucleotide overhangs on the 3' ends, or may be blunt-ended. Each strand has a 5' phosphate group and a 3' hydroxyl group. Most siRNA molecules are 18 to 30 (e.g., 21 to 30) nucleotides in length, however a skilled practitioner may vary this sequence length (e.g., to increase or decrease the overall level of gene silencing).

Almost any gene for which the sequence is known can thus be targeted based on sequence complementarity with an appropriately tailored siRNA. See, for example, Zamore et al., Cell 101:25-33, 2000; Bass, Nature 411:428-429, 2001; Elbashir et al., Nature 411:494-498, 2001; and PCT Publication Nos. WO 00/44895, WO 01/36646, WO 99/32619, WO 00/01846, WO 01/29058, WO 99/07409, and WO 00/44914. Methods for preparing a siRNA molecule are known in the art and described in, for example, U.S. Pat. No. 7,078,196. Accordingly, one of skill in the art would understand that a wide variety of different siRNA molecules may be used to target a specific gene or transcript. In certain embodiments, siRNA molecules according to the invention are double-stranded and 16-30 or 18-25 nucleotides in length, including each integer in between. In one embodiment, an siRNA is 21 nucleotides in length. In certain embodiments, siRNAs have 0-7 nucleotide 3' overhangs or 0-4 nucleotide 5' overhangs. In one embodiment, a siRNA molecule has a two nucleotide 3' overhang. In one embodiment, a siRNA is 21 nucleotides in length with two nucleotide 3' overhangs (e.g., they contain a 19 nucleotide complementary region between the sense and antisense strands). In certain embodiments, the overhangs are UU or dTdT 3' overhangs.

Generally, siRNA molecules are completely complementary to one strand of a target DNA molecule, since even single base pair mismatches have been shown to reduce silencing. In other embodiments, siRNAs may have a modified backbone composition, such as, for example, 2'-deoxy- or 2'-O-methyl modifications. However, in preferred embodiments, the entire strand of the siRNA is not made with either 2' deoxy or 2'-O-modified bases. In one embodiment, siRNA target sites are selected by scanning the target mRNA transcript sequence for the occurrence of AA dinucleotide sequences. Each AA dinucleotide sequence in combination with the 3' adjacent approximately 19 nucleotides are potential siRNA target sites. In one embodiment, siRNA target sites are preferentially not located within the 5' and 3' untranslated regions (UTRs) or regions near the start codon (within approximately 75 bases), since proteins that bind regulatory regions may interfere with the binding of the siRNP endonuclease complex (Elshabir et al., Nature 411: 494-498, 2001; Elshabir et al., EMBO J. 20:6877-6888, 2001). In addition, potential target sites may be compared to an appropriate genome database, such as BLASTN 2.0.5, and potential target sequences with significant homology to other coding sequences eliminated.

A short hairpin RNA (shRNA) molecule may also be used in the methods of the invention to target one or more components of the JAK/STAT pathway, the TLP pathway, the NF-κB pathway, PKR pathway, the MAP kinase pathway, and/or the TBK1/IKKe pathway. shRNA are single-stranded RNA molecules in which a tight hairpin loop structure is present, allowing complementary nucleotides within the same strand to form bonds. shRNA can exhibit reduced sensitivity to nuclease degradation as compared to siRNA. Once inside a target cell, shRNA are processed and effect gene silencing by the same mechanism described above for siRNA. In certain embodiments, they may contain variable stem lengths, typically from 19 to 29 nucleotides in length, or any number in between. In certain embodiments, hairpins contain 19 to 21 nucleotide stems, while in other embodiments, hairpins contain 27 to 29 nucleotide stems. In certain embodiments, loop size is between 4 to 23 nucleotides in length, although the loop size may be larger than 23 nucleotides without significantly affecting silencing activity. shRNA molecules may contain mismatches, for example G-U mismatches between the two strands of the shRNA stem without decreasing potency. In certain embodiments, shRNAs are designed to include one or several G-U pairings in the hairpin stem to stabilize hairpins during propagation in bacteria, for example. However, complementarity between the portion of the stem that binds to the target mRNA (antisense strand) and the mRNA is typically required, and even a single base pair mismatch is this region may abolish silencing. 5' and 3' overhangs are not required, since they do not appear to be critical for shRNA function, although they may be present (Paddison et al., Genes & Dev. 16(8):948-958, 2002).

Double-stranded RNA (dsRNA) can also be used in the methods of the invention to target one or more components of the JAK/STAT pathway, the TLP pathway, the NF-κB pathway, PKR pathway, the MAP kinase pathway, and/or the TBK1/IKKe pathway. Any double-stranded RNA that can be cleaved in cell into siRNA molecules that target a specific mRNA can be used. Methods of preparing dsRNA for use as RNAi agents are described in, for example, U.S. Pat. No. 7,056,704.

MicroRNAs (miRNA) can also be used in the invention. miRNA are single-stranded RNA molecules that can silence a target gene (e.g., a gene encoding a protein that is a component involved in one or more of the JAK/STAT pathway, the TLP pathway, the NF-κB pathway, PKR pathway, the MAP kinase pathway, and/or the TBK1/IKKe pathway) using the same or similar mechanisms as siRNA and shRNA agents. miRNA molecules of 17 to 25 (e.g., 21 to 23) nucleotides in length are often used, as these are generally the most effective for gene silencing; however, a skilled practitioner may vary the sequence length as desired.

The nucleic acid can be an antisense oligonucleotide directed to a target polynucleotide. Antisense oligonucleotides are single strands of DNA or RNA that are complementary to a chosen sequence. In the case of antisense RNA, they prevent translation of complementary RNA strands by binding to it. Antisense DNA can be used to target a specific, complementary (coding or non-coding) RNA. If binding takes places this DNA/RNA hybrid can be degraded by the enzyme RNase H. In a particular embodiment, antisense oligonucleotides contain from about 10 to about 50 nucleotides, more preferably about 15 to about 30 nucleotides. The term also encompasses antisense oligonucleotides that may not be exactly complementary to the desired target gene. Thus, antisense agents can be utilized in methods of the invention in instances where non-target specific-activities are found with antisense, or where an antisense sequence containing one or more mismatches with the target sequence is the most preferred for a particular use.

Antisense oligonucleotides have been demonstrated to be effective and targeted inhibitors of protein synthesis, and, consequently, can be used to specifically inhibit protein synthesis by a targeted gene (e.g., a pathogenic APOL1 polypeptide, but preferably not a common APOL1 polypeptide or one or more genes encoding protein components involved in the JAK/STAT pathway, the TLP pathway, the NF-κB pathway, PKR pathway, the MAP kinase pathway, and/or the TBK1/IKKe pathway). The efficacy of antisense oligonucleotides for inhibiting protein synthesis is well established. For example, the synthesis of polygalacturonase and the muscarine type 2 acetylcholine receptor are inhibited by antisense oligonucleotides directed to their respective mRNA sequences (U.S. Pat. Nos. 5,739,119 and 5,759,829). Further, examples of antisense inhibition have been demonstrated with the nuclear protein cyclin, the multiple drug resistance gene (MDG1), ICAM-1, E-selectin, STK-1, striatal GABAA receptor and human EGF (see e.g., Jaskulski et al., *Science* 240(4858):1544-1546, 1988; Vasanthakumar et al., *Cancer Commun.* 1(4):225-232, 1989; Penis et al., *Brain Res Mol Brain Res.* 57(2):310-20, 1998; and U.S. Pat. Nos. 5,801,154; 5,789,573; 5,718,709; and 5,610,288). Furthermore, antisense constructs have also been described that inhibit and can be used to treat a variety of abnormal cellular proliferations, e.g. cancer (U.S. Pat. Nos. 5,747,470; 5,591,317; and 5,783,683).

Methods of producing antisense oligonucleotides are known in the art and can be readily adapted to produce an antisense oligonucleotide that targets any polynucleotide sequence. Selection of antisense oligonucleotide sequences specific for a given target sequence is based upon analysis of the chosen target sequence and determination of secondary structure, Tm, binding energy, and relative stability. Antisense oligonucleotides may be selected based upon their relative inability to form dimers, hairpins, or other secondary structures that would reduce or prohibit specific binding to the target mRNA in a host cell. Highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software (Molecular Biology Insights) and/or the BLASTN 2.0.5 algorithm software (Altschul et al., *Nucleic Acids Res.* 25(17):3389-3402, 1997).

According to another embodiment of the invention, nucleic acid-lipid particles can be associated with ribozymes. Ribozymes are RNA-protein complexes having specific catalytic domains that possess endonuclease activity (Kim et al., *Proc Natl Acad Sci USA* 84(24):8788-8792, 1987; Forster et al., *Cell* 49(2):211-220, 1987). For example, a large number of ribozymes accelerate phosphoester transfer reactions with a high degree of specificity, often cleaving only one of several phosphoesters in an oligonucleotide substrate. This specificity has been attributed to the requirement that the substrate bind via specific base-pairing interactions to the internal guide sequence ("IGS") of the ribozyme prior to chemical reaction. The enzymatic nucleic acid molecule may be formed in a hammerhead, hairpin, a hepatitis δ virus, group I intron or RNaseP RNA (in association with an RNA guide sequence) or Neurospora VS RNA motif, for example. Specific examples of hammerhead motifs are described by Rossi et al., *Nucleic Acids Res.* 20(17):4559-4565, 1992. Examples of hairpin motifs are described by Hempel et al. (Eur. Pat. Appl. Publ. No. EP 0360257), Hampel et al., *Biochemistry* 28(12):4929-4933, 1989; Hampel et al., *Nucleic Acids Res.* 18(2):299-304, 1990, and U.S. Pat. No. 5,631,359; and an example of the Group I intron is described in U.S. Pat. No. 4,987,071. Ribozymes may be designed as described in Int. Pat. Appl. Publ. No. WO 93/23569 and Int. Pat. Appl. Publ. No. WO 94/02595, each specifically incorporated herein by reference, and synthesized to be tested in vitro and in vivo, as described therein. Ribozyme activity can be optimized by altering the length of the ribozyme binding arms or chemically synthesizing ribozymes with modifications that prevent their degradation by serum ribonucleases (see e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem loop bases to shorten RNA synthesis times and reduce chemical requirements.

A variety of methods are available for the introduction (e.g., transfection) of nucleic acid molecules (e.g., RNAi agents) into mammalian cells. For example, there are several commercially-available transfection reagents useful for lipid-based transfection of siRNAs including, but not limited to, TransIT-TKO™ (Mirus, Catalog No. MIR 2150), Transmessenger™ (Qiagen, Catalog No. 301525), Oligofectamine™ and Lipofectamine™ (Invitrogen, Catalog No. MIR 12252-011 and Catalog No. 13778-075), siPORT™ (Ambion, Catalog No. 1631), and DharmaFECT™ (Fisher Scientific, Catalog No. T-2001-01). Agents are also commercially available for electroporation-based methods for transfection of siRNA, such as siPORTer™ (Ambion, Catalog No. 1629). Microinjection techniques may also be used. The nucleic acid molecule may also be transcribed from an expression construct introduced into the cells, where the expression construct includes a coding sequence for transcribing the nucleic acid molecule operably linked to one or more transcriptional regulatory sequences. Where desired, plasmids, vectors, or viral vectors can also be used for the delivery of the nucleic acid molecule, and such vectors are known in the art. Additional methods are known in the art and are described, for example, in U.S. Patent Application Publication No. 2006/0058255.

Any of the RNAi molecules described herein may be modified or substituted with nucleotide analogs, e.g., as described herein. RNAi agents may be capable of silencing any gene where a reduction in expression of that gene is therapeutically beneficial, e.g., by resulting in a reduction of APOL1 polypeptide expression, or in the expression of a gene encoding a component involved in the JAK/STAT pathway, the TLP pathway, the NF-κB pathway, PKR pathway, the MAP kinase pathway, and/or the TBK1/IKKe pathway, the silencing of which mediates a decrease in expression of a pathogenic APOL1 polypeptide.

Modified Nucleic Acids for Use in the RNAi Molecules of the Invention

Modified nucleic acids, including modified DNA or RNA molecules, may be used in the in place of naturally occurring nucleic acids in the RNAi polynucleotides described herein. Modified nucleic acids can improve the half-life, stability, specificity, delivery, solubility, and nuclease resistance of the polynucleotides described herein. For example, siRNA agents can be partially or completed composed of nucleotide analogs that confer the beneficial qualities described above. As described in Elmén et al. (*Nucleic Acids Res.* 33:439-447, 2005), synthetic, RNA-like nucleotide analogs (e.g., locked nucleic acids (LNA)) can be used to construct siRNA molecules that exhibit silencing activity against a target gene product.

Modified nucleic acids include molecules in which one or more of the components of the nucleic acid, namely sugars, bases, and phosphate moieties, are different from that which occurs in nature, preferably different from that which occurs in the human body. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone.

Antisense, siRNA, and other oligonucleotides useful in this invention include, but are not limited to, oligonucleotides containing modified backbones or non-natural internucleoside linkages. Oligonucleotides having modified backbones include those that retain a phosphorus atom in the backbone and those that do not have a phosphorus atom in the backbone. Modified oligonucleotides that do not have a phosphorus atom in their internucleoside backbone can also be considered to be oligonucleosides. Modified oligonucleotide backbones include, for example, phosphorothioates, chiral phosphorothioates, phosphorodithioates, phosphotri-esters, aminoalkylphosphotri-esters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, phosphoroselenate, methylphosphonate, or O-alkyl phosphotriester linkages, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included. Representative United States patents that teach the preparation of the above linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

In certain embodiments, modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include, e.g., those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative United States patents that describe the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

The phosphorothioate backbone modification, where a non-bridging oxygen in the phosphodiester bond is replaced by sulfur, is one of the earliest and most common means deployed to stabilize nucleic acid drugs against nuclease degradation. In general, it appears that PS modifications can be made extensively to both siRNA strands without much impact on activity (Kurreck, *Eur. J. Biochem.* 270:1628-44, 2003). In particular embodiments, the PS modification is usually restricted to one or two bases at the 3' and 5' ends. The boranophosphate linker can be used to enhance siRNA activity while having low toxicity (Hall et al., *Nucleic Acids Res.* 32:5991-6000, 2004).

Other useful nucleic acids derivatives include those nucleic acids molecules in which the bridging oxygen atoms (those forming the phosphoester linkages) have been replaced with —S—, —NH—, —$CH_2$—, and the like. In certain embodiments, the alterations to the antisense, siRNA, or other nucleic acids used will not completely affect the negative charges associated with the nucleic acids. Thus, the present invention contemplates the use of antisense, siRNA, and other nucleic acids in which a portion of the linkages are replaced with, for example, the neutral methyl phosphonate or phosphoramidate linkages. When neutral linkages are used, in certain embodiments, less than 80% of the nucleic acid linkages are so substituted, or less than 50% of the linkages are so substituted.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain nucleobases are particularly useful for increasing the binding affinity of the oligomeric compounds of the invention, including 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications 1993, CRC Press, Boca Raton, pages 276-278). These may be combined, in particular embodiments, with 2'-O-methoxyethyl sugar modifications. United States patents that teach the preparation of certain of these modified nucleobases as well as other modified nucleobases include, but are not limited to, the above noted U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941.

Exemplary sugar modifications include modifications to the 2'-OH of the RNA sugar ring, which provides a convenient chemically reactive site. Exemplary modifications include the 2'-F and 2'-OMe modification, which can be restricted to less than 4 nucleotides per strand (Holen et al., *Nucleic Acids Res* 31:2401-2407, 2003). The 2'-O-MOE is most effective in siRNA when modified bases are restricted to the middle region of the molecule (Prakash et al., *J. Med. Chem.* 48:4247-4253, 2005).

Modified oligonucleotides may also contain one or more substituted sugar moieties. For example, the invention includes oligonucleotides that comprise one of the following at the 2' position: OH; F; O—, S—, or N-alkyl, O-alkyl-O-alkyl, O—, S—, or N-alkenyl, or O—, S- or N-alkynyl, wherein the alkyl, alkenyl and alkynyl may be substituted or unsubstituted $C_{1-10}$ alkyl or $C_{2-10}$ alkenyl and alkynyl. Particularly preferred are $O[(CH_2)_nO]_mCH_3$, $O(CH_2)_nOCH_3$, $O(CH_2)_2ON(CH_3)_2O(CH_2)_nNH_2$, $O(CH_2)_nCH_3$, $O(CH_2)_nONH_2$, and $O(CH_2)_nON[(CH_2)_nCH_3)]=$, where n and m are from 1 to about 10. Other preferred oligonucleotides comprise one of the following at the 2' position: $C_{1-10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy (2'-O—$CH_2CH_2OCH_3$, also known as 2'-O-(2-methoxyethyl) or 2'-MOE) (Martin et al., *Helv. Chim. Acta* 78:486-504, 1995), i.e., an alkoxyalkoxy group. Other modifications include 2'-dimethylaminooxyethoxy, i.e., a $O(CH_2)_2ON(CH_3)_2$ group, also known as 2'-DMAOE, and 2'-dimethylaminoethoxyethoxy (2'-DMAEOE). Additional modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920.

In other oligonucleotide mimetics, both the sugar and the internucleoside linkage, i.e., the backbone, of the nucleotide units are replaced with novel groups, although the base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262. Further teaching of PNA compounds can be found in Nielsen et al., *Science* 254, 1497-1500 (1991).

Particular embodiments of the invention are oligonucleotides with phosphorothioate backbones and oligonucleosides with heteroatom backbones, and in particular $CH_2NHOCH_2$, $CH_2N(CH_3)OCH_2$-(referred to as a methylene(methylimino) or MMI backbone), $CH_2ON(CH_3)CH_2$, $CH_2N(CH_3)N(CH_3)CH_2$, and $ON(CH_3)CH_2CH_2$ (wherein the native phosphodiester backbone is represented as $OPOCH_2$) of U.S. Pat. No. 5,489,677; the amide backbones of U.S. Pat. No. 5,602,240; and the morpholino backbone structures U.S. Pat. No. 5,034,506.

Treatment During Apheresis

The invention also features methods of treating a subject (e.g., a subject having or at risk of developing a renal disease) by contacting the blood of the subject during extracorporeal apheresis methods with one or more of the agents of the invention (e.g., one or more agents that target one or more components of the JAK/STAT pathway, the TLP pathway, the NF-κB pathway, PKR pathway, the MAP kinase pathway, and/or the TBK1/IKKe pathway).

Generally, apheresis includes the removal or withdrawal of blood from the subject's body, removal of one or more components from the blood, and transfusion of the remaining blood back into the subject's body. In the present invention, one or more agents of the invention (e.g., one or more agents that target one or more components of the JAK/STAT pathway, the TLP pathway, the NF-κB pathway, PKR pathway, the MAP kinase pathway, and/or the TBK1/IKKe pathway) are contacted to the blood of a subject during apheresis.

Apheresis procedures and equipment are known in the art and can be used in the present invention. In one example, once the patient's blood is removed from a vein in the arm, the plasma is separated from the rest of the blood using a membrane plasma filter. Either the plasma or the blood can be contacted with one or more of the compositions of the invention and then recombined and returned to the patient.

In yet another example, blood from the patient is circulated extra-corporeally using standard apheresis equipment. The blood is separated into the cellular elements (red blood cells, white blood cells and platelets) and fluid (plasma) elements using differential centrifugation or a membrane filter. The plasma is then pumped through the targeted apheresis device where it can be contacted with one or more of the compositions of the invention. Alternatively, the other blood components can be contacted with one or more of the compositions of the invention. After the contacting step, the plasma is then mixed with the cellular blood elements and returned to the patient. In one embodiment, the pH of the blood is restored to normal biological levels prior to returning to the subject.

Additional Therapies

The agents of the invention (e.g., one or more agents that target one or more components of the JAK/STAT pathway, the TLP pathway, the NF-κB pathway, PKR pathway, the MAP kinase pathway, and/or the TBK1/IKKe pathway) may be administered alone or in combination with other known therapies for the treatment of renal disease. For example, a subject treated with an agent of the invention (e.g., one or more agents that target one or more components of the JAK/STAT pathway, the TLP pathway, the NF-κB pathway, PKR pathway, the MAP kinase pathway, and/or the TBK1/IKKe pathway) may also be treated with a blood pressure medication, a steroid, and/or an immunosuppressive agent. Examples of therapeutics include blood pressure medications (e.g., a diuretic (e.g., chlorthalidone, chlorothiazide, furosemide, hydrochlorothiazide, indapamide, metolazone, amiloride hydrochloride, spironolactone, triamterene, bumetanide, or a combination thereof), an alpha adrenergic antagonist (e.g., alfuzosin, doxazosin, prazosin, terazosin, or tamsulosin, or a combination thereof), a central adrenergic inhibitor (e.g., clonidine, guanfacine, or methyldopa, or a combination thereof), an angiotensin converting enzyme (ACE) inhibitor (e.g., benazepril, captopril, enalapril, fosinopril, lisinopril, moexipril, perindopril, quinapril, ramipril, or trandolapril, or combinations thereof), an angiotensin II receptor blocker (e.g., candesartan, eprosartan, irbesartan, losartan, olmesartan, telmisartan, or valsartan, or combinations thereof), an alpha blocker (e.g., doxazosin, prazosin, or terazosin, or a combination thereof), a beta blocker (e.g., acebutolol, atenolol, betaxolol, bisoprolol, carteolol, metoprolol, nadolol, nebivolol, penbutolol, pindolol, propranolol, solotol, or timolol, or a combination thereof), a calcium channel blocker (e.g., amlodipine, bepridil, diltiazem, felodipine, isradipine, nicardipine, nifedipine, nisoldipine, or verapamil, or combination thereof), a vasodilator (e.g., hydralazine or minoxidil, or combination thereof), and a renin inhibitor (e.g., aliskiren), or combinations thereof), a steroid (e.g., a corticosteroid, such as cortisone, prednisone, methylprednisolone, or prednisolone), or an anabolic steroid (anatrofin, anaxvar, annadrol, bolasterone, decadiabolin, decadurabolin, dehydropiandrosterone (DHEA), delatestryl, dianiabol, dihydrolone, durabolin, dymethazine, enoltestovis, equipose, gamma hydroxybutyrate, maxibolin, methatriol, methyltestosterone, parabolin, primobolin, quinolone, therabolin, trophobolene, and winstrol), or an immunosuppressive agent, such as a glucocorticoid, a cytostatic, an antibody, or an anti-immunophilin and/or mychophenolate mofetil (MMF), FK-506, azathioprine, cyclophosphamide, methotrexate, dactinomycin, antithymocyte globulin (AT-GAM), an anti-CD20-antibody, a muromonoab-CD3 antibody, basilizimab, daclizumab, cyclosporin, tacrolimus, voclosporin, sirolimus, an interferon, infliximab, etanercept, adalimumab, fingolimod, and/or myriocin).

Administration and Dosage

Agents of the invention (e.g., one or more agents that target one or more components of the JAK/STAT pathway, the TLP pathway, the NF-κB pathway, PKR pathway, the MAP kinase pathway, and/or the TBK1/IKKe pathway) may be administered in methods of the invention in a therapeutically effective amount. In some examples, a therapeutically effective amount of an agent of the invention (e.g., one or more agents that target one or more components of the JAK/STAT pathway, the TLP pathway, the NF-κB pathway, PKR pathway, the MAP kinase pathway, and/or the TBK1/IKKe pathway) includes an amount, per dose, in the range of about 0.01 mg/kg to about 1000 mg/kg (such as about 0.01 mg/kg to 1000 mg/kg, 0.05 mg/kg to 500 mg/kg, 0.1 mg/kg to 1000 mg/kg, about 10 mg/kg to 500 mg/kg, about 10 mg/kg to 100 mg/kg, about 50 mg/kg to 500 mg/kg, or about 100 mg/kg to 1000 mg/kg). Administration can be accomplished by single or multiple doses and depends on the specific agent being administered and the administration route. Doses are determined for each particular case using standard methods in accordance with factors unique to the patient, including age, weight, general state of health, and other factors that can influence the efficacy of the compound(s) of the invention. The dose required will vary from subject to subject depending on the species, age, weight and general condition of the subject, the particular therapeutic agent being used and its mode of administration. For example, preferred doses can be 0.1-1 mg/kg by inhalation, desirably 0.5-10 mg/kg per day by oral administration, and desirably 0.1-1 mg/kg body weight per day by intravenous administration. Generally, dosage levels of an agent of the invention of between 0.1 µg/kg to 100 mg/kg of body weight are administered daily, weekly, monthly, or yearly as a single dose or divided into multiple doses (e.g., 2-12 doses per day, week, month, or year), or as needed. Preferably, the general dosage range is between 250 µg/kg to 50.0 mg/kg of body weight per day. Wide variations in the needed dosage are to be expected in view of the differing efficiencies of the various routes of administration. For instance, oral administration generally would be expected to require higher dosage levels than administration by intravenous injection. Variations in these dosage levels can be adjusted using standard empirical routines for optimization, which are well known in the art. In general, the precise therapeutically effective dosage will be determined by the attending physician in consideration of the above-identified factors. It will be appreciated that these dosages are examples only, and an appropriate dose can be determined by one of ordinary skill in the art using only routine experimentation.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Pharmaceutical formulations of a therapeutically effective amount of an agent of the invention (e.g., one or more agents that target one or more components of the JAK/STAT pathway, the TLP pathway, the NF-κB pathway, PKR pathway, the MAP kinase pathway, and/or the TBK1/IKKe pathway), or pharmaceutically acceptable salts thereof, can be administered orally, parenterally (e.g., as an intramuscular, intraperitoneal, intravenous, intraarterial, or subcutaneous injection), by inhalation, intradermally, by optical drops, by implant, nasally, vaginally, rectally, sublingually, or topically, and may be in admixture with a pharmaceutically acceptable carrier adapted for the route of administration. The choice of vehicle and the content of active substance in the vehicle are generally determined in accordance with the solubility and chemical properties of the product, the particular mode of administration, and the provisions to be observed in pharmaceutical practice. For example, excipients such as lactose, sodium citrate, calcium carbonate, and dicalcium phosphate and disintegrating agents such as starch, alginic acids, and certain complex silicates combined with lubricants (e.g., magnesium stearate, sodium lauryl sulfate, and talc) may be used for preparing tablets. To prepare a capsule, it is advantageous to use lactose and high molecular weight polyethylene glycols. When aqueous suspensions are used, they may contain emulsifying agents that facilitate suspension. Diluents such as sucrose, ethanol, polyethylene glycol, propylene glycol, glycerol, chloroform, or mixtures thereof may also be used.

An agent of the invention (e.g., an agent that targets one or more components of the JAK/STAT pathway, the TLP pathway, the NF-κB pathway, PKR pathway, the MAP kinase pathway, and/or the TBK1/IKKe pathway) may also be administered in the form of liposome delivery systems, such as small unilamellar vesicles, large unilamellar vesicles, and multilamellar vesicles. Liposomes can be formed from a variety of lipids, such as cholesterol, stearylamine, or phosphatidylcholines.

Methods well known in the art for making formulations are found, for example, in *Remington's Pharmaceutical Sciences* (18$^{th}$ edition), ed. A. Gennaro, 1990, Mack Publishing Company, Easton, Pa. Compositions intended for oral use may be prepared in solid or liquid forms according to any method known to the art for the manufacture of pharmaceutical compositions. The compositions may optionally contain sweetening, flavoring, coloring, perfuming, and/or preserving agents in order to provide a more palatable preparation. Solid dosage forms for oral administration include capsules, tablets, pills, powders, and granules. In such solid forms, the active agent is admixed with at least one inert pharmaceutically acceptable carrier or excipient. These may include, for example, inert diluents, such as calcium carbonate, sodium carbonate, lactose, sucrose, starch, calcium phosphate, sodium phosphate, or kaolin. Binding agents, buffering agents, and/or lubricating agents (e.g., magnesium stearate) may also be used. Tablets and pills can additionally be prepared with enteric coatings.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. Liquid dosage forms for oral administration include pharmaceutically acceptable emulsions, solutions, suspensions, syrups, and soft gelatin capsules. These forms contain inert diluents commonly used in the art, such as water or an oil medium. Besides such inert diluents, compositions can also include adjuvants, such as wetting agents, emulsifying agents, and suspending agents.

Formulations for parenteral administration include sterile aqueous or non-aqueous solutions, suspensions, or emulsions. Examples of suitable vehicles include propylene glycol, polyethylene glycol, vegetable oils, gelatin, hydrogenated naphthalenes, and injectable organic esters, such as ethyl oleate. Such formulations may also contain adjuvants, such as preserving, wetting, emulsifying, and dispersing agents. Biocompatible, biodegradable lactide polymer, lactide/glycolide copolymer, or polyoxyethylene-polyoxypropylene copolymers may be used to control the release of the compounds. Other potentially useful parenteral delivery systems for the agents of the invention include ethylene-vinyl acetate copolymer particles, osmotic pumps, implantable infusion systems, and liposomes.

Liquid formulations can be sterilized by, for example, filtration through a bacteria-retaining filter, by incorporating sterilizing agents into the compositions, or by irradiating or heating the compositions. Alternatively, they can also be manufactured in the form of sterile, solid compositions, which can be dissolved in sterile water or some other sterile injectable medium immediately before use.

Compositions for rectal or vaginal administration are preferably suppositories, which may contain, in addition to active substances, excipients such as cocoa butter or a suppository wax. Compositions for nasal or sublingual administration are also prepared with standard excipients known in the art. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops or spray, or as a gel.

The amount of active agent of the invention can be varied. One skilled in the art will appreciate that the exact individual dosages may be adjusted somewhat depending upon a variety of factors, including the ingredient being administered, the time of administration, the route of administration, the nature of the formulation, the rate of excretion, the nature of the subject's conditions, and the age, weight, health, and gender of the patient. In addition, the severity of the condition targeted by an agent of the invention will also have an impact on the dosage level.

An agent of the invention can be administered in a sustained release composition, such as those described in, for example, U.S. Pat. Nos. 5,672,659 and 5,595,760, hereby incorporated by reference, or as a liposomal formulation. The use of immediate or sustained release compositions depends on the type of condition being treated. If the condition consists of an acute or over-acute disorder, a treatment with an immediate release form will be preferred over a prolonged release composition. Alternatively, for preventative or long-term treatments, a sustained released composition will generally be preferred.

Where sustained release administration of the agent (e.g., a compound, an antibody, peptide, or nucleic acid molecule) is desired in a formulation with release characteristics suitable for the treatment of any disease or disorder requiring administration of the agent (e.g., treatment of renal disease), microencapsulation of the agent is contemplated. Microencapsulation of recombinant proteins for sustained release has been successfully performed with human growth hormone (rhGH), interferon-(rhIFN−), interleukin-2, and MN rgp120 (Johnson et al., *Nat. Med.* 2: 795-799, 1996; Yasuda, *Biomed. Ther.* 27: 1221-1223, 1993; Hora et al., *Bio/Tech-* nology 8: 755-758 1990; Cleland, "Design and Production of Single Immunization Vaccines Using Polylactide Polyglycolide Microsphere Systems," in "Vaccine Design: The Subunit and Adjuvant Approach," Powell and Newman, Eds., Plenum Press: New York, pp. 439-462, 1995; WO 97/03692; WO 96/40072; WO 96/07399; and U.S. Pat. No. 5,654,010, hereby incorporated by reference).

The sustained-release formulations may also include those developed using poly-lactic-coglycolic acid (PLGA) polymer. The degradation products of PLGA, lactic and glycolic acids, can be cleared quickly from the human body. Moreover, the degradability of this polymer can be adjusted from months to years depending on its molecular weight and composition (see, e.g., Lewis, "Controlled release of bioactive agents from lactide/glycolide polymer," in M. Chasin and Dr. Langer (Eds.), Biodegradable Polymers as Drug Delivery Systems (Marcel Dekker: New York, pp. 1-41, 1990)).

An agent of the invention can be prepared in any suitable manner. The agent may be isolated from naturally-occurring sources, or produced synthetically, identified from a library, or produced by a combination of these methods.

Assessment of Therapy

After therapeutic treatment with the compositions of the invention described herein, the efficacy of the treatment may be assessed by a number of methods, such as assays that measure hypoalbuminemia (low serum albumin) in the blood, a reduction in symptoms of hyperlipidemia and hypertension (high blood pressure), a reduction in edema (fluid retention), a reduction in inflammation in the kidney (e.g., in the nephron), a reduction in protein in the urine (proteinuria), a reduction of blood in the uring (hematuria), and/or an increase in renal function. Tests that can be performed include urinalysis, blood tests (for, e.g., cholesterol), and kidney biopsy (e.g., a reduction in sclerosis (scarring) of the glomerulus). Efficacy may also be indicated by an improvement in or resolution of one or more symptoms of renal disease or in a reduced need of, or frequency of, dialysis.

Diagnostics

A patient that may be in need of one or more of the treatment methods described herein can be identified by detecting one or more APOL1 risk alleles in the patient (e.g., one or more of the G1a, G1 b, G1, G2, or G3 risk alleles described herein). Preferably, the patient includes two or more APOL1 risk alleles. In other embodiments, the subject is of African or Hispanic ancestry. For example, subjects of African or Hispanic ancestry that have at least two (or more) of APOL1 gene risk alleles exhibit a significantly increased risk of developing renal disease. Thus, these subjects may be assayed for the presence of a wild type allele (relative to an APOL1 gene risk allele) as a means for determining whether the subject has a moderate or increased risk of renal disease. For example, a subject that is heterozygous at a given locus for one or more of the APOL1 gene risk alleles may have a greater risk of renal disease relative to a subject lacking any APOL1 gene risk alleles, and thus may be more likely to benefit from treatment using one or more of the methods or compositions described herein. A subject that is homozygous at a given locus for one or more APOL1 gene risk alleles may have a greater risk of renal disease, relative to a subject that is heterozygous for an APOL1 gene risk allele at that locus or a subject that lacks any risk alleles in an APOL1 gene, and thus may be more likely to benefit from treatment using one or more of the methods or compositions described herein. The presence of two or more (e.g., three, four, or more) risk alleles at different loci further increases the likelihood of renal disease in a subject. Thus a subject having two or more (e.g., three, four, or more) risk alleles at different loci is likely to benefit from treatment using one or more of the methods or compositions described herein.

Thus, the present invention also features a method of diagnosing a subject that is likely to benefit from one or more of the treatment methods described herein by using any number of methods known in the art. For example, these can include, genomic sequencing assay, polymerase chain reaction assay, fluorescence in situ hybridization assay, immunoassay, or using one or more of the methods or kits described in, e.g., PCT/US2011/032924, which is incorporated herein by reference, to identify the presence or absence of one or more APOL1 risk alleles in the subject. Once the subject has been identified as having one or more (or two, three, or four, or more) APOL1 risk alleles at one or more loci, and thus to have or to be at a greater risk of developing a renal disease, the subject may be administered one or more of the compositions of the invention in order to treat (prophylactically or therapeutically) the renal disease or to reduce one or more of the symptoms of the renal disease.

The invention also provides for a diagnostic test kit for detecting the presence of one or more APOL1 risk alleles. The invention also provides a kit for treating a subject once a diagnosis that the subject has or is at risk of developing renal disease has been made. The kit may include the diagnostic reagents and instructions for detecting the presence of an APOL1 risk allele only or the diagnostic reagents and one or more agents of the invention (e.g., one or more agents that target one or more components of the JAK/STAT pathway, the TLP pathway, the NF-κB pathway, PKR pathway, the MAP kinase pathway, and/or the TBK1/IKKe pathway) for treating the renal disease and, optionally, instructions for performing the diagnosis and the treatment methods, or only agents pf the invention for treating the renal disease and, optionally, instructions for the treatment methods. The kit may also include one or more other therapeutic agents, such as a blood pressure medication, a steroid, or an antiinflammatory agent.

EXAMPLES

In order to make the methods of the invention clearer, the following examples are presented. These examples are only for illustrative purposes and should not be interpreted in any way as limitations on the compositions and uses of this invention.

Example 1: Severe and Widespread Liver Injury Caused by G1 Risk Variant

Wild type and risk variant APOL1 cDNA were injected into mice via hydrodynamic gene delivery (FIG. 1). The cDNA was taken up and expressed by the liver. Mice injected with wild type APOL1 showed only subtle signs of liver injury, whereas mice injected with a risk variant APOL1 had severe and widespread necrosis, indicating greater toxicity of the risk variants. These findings support an unusual gain-of-function model despite recessive mode of inheritance, a situation rare in biology and to our knowledge unique for a common disease.

Example 2: Variation in Human APOL1 Expression Between Individuals

Figure 2:
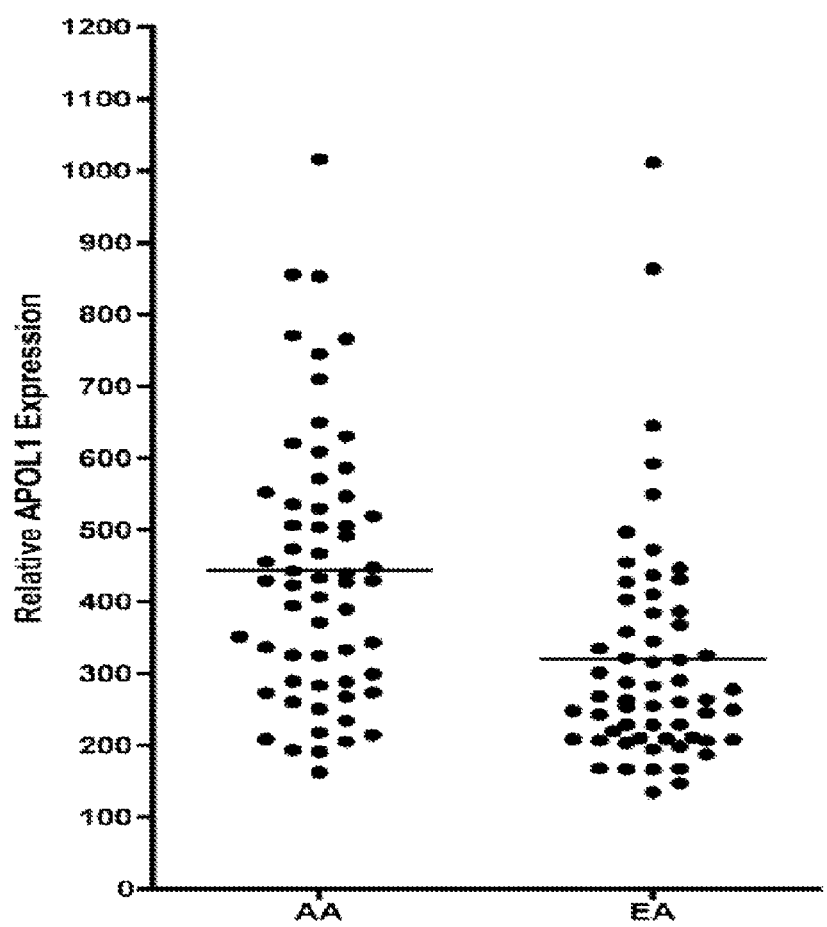
FIG. 2 is a graph showing APOL1 mRNA expression levels in 60 Africans (AA) and Europeans (EA). Expression levels differ widely between individuals.

Not all individuals with the APOL1 risk genotype develop kidney disease. If APOL1 mediated renal disease is caused by a gain-of-function mutation, then expression differences may determine which individuals will develop kidney disease. Gene expression profiling studies of lymphoblasts from Africans and Europeans (FIG. 2) shows that Africans have on average higher APOL1 gene expression levels than Europeans. More striking are the expression differences between individuals within each group.

Example 3: Inflammatory Factors Cause Log-Fold Upregulation of APOL1

Figure 3A:
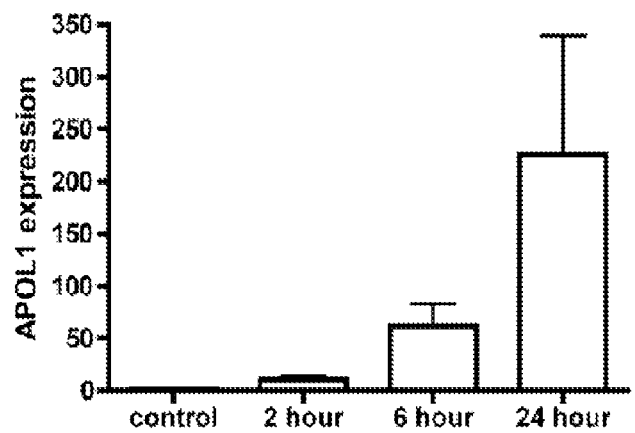
FIGS. 3A and 3B are graphs showing APOL1 mRNA expression in endothelial cells after stimulation with interferon gamma (FIG. 3A) or interferon beta (FIG. 3B). Similar effects were observed for endothelial cells treated with interferon alpha, and for podocytes treated with interferon alpha, beta, or gamma.
Figure 3B:
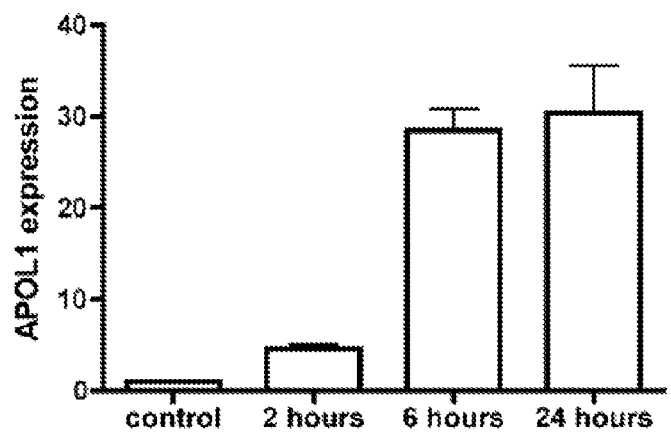

Interferons cause log-fold upregulation of APOL1 gene expression in several cell types. Both type 1 (alpha and beta) interferons and type 2 (gamma) interferon greatly amplifies APOL1 expression in both endothelial cells and podocytes. FIG. 3A shows interferon gamma upregulates APOL1 in endothelial cells by up to 200-fold, whereas interferon beta (FIG. 3B) upregulates APOL1 in endothelial cells by up to 30-fold.

Example 4: JAK Inhibitors Block the Potentially Pathologic Upregulation of APOL1

Figure 4A:
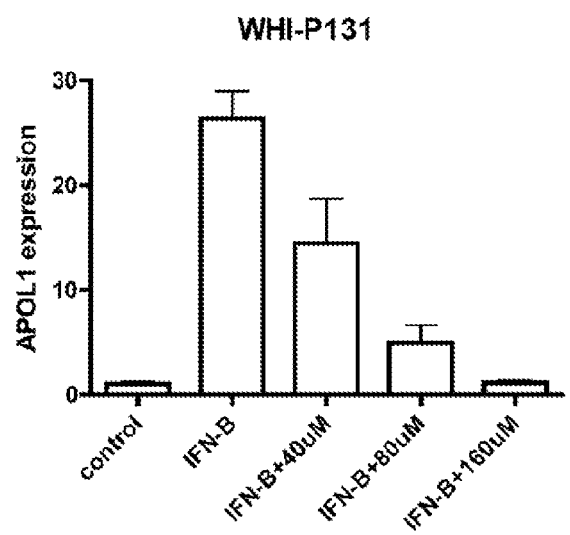
FIGS. 4A, 4B, and 4C are graphs showing APOL1 mRNA expression in endothelial cells treated with interferon beta and various Jak kinase inhibitors: WHI-P131 (FIG. 4A), INCB018424 (FIG. 4B), and TG101348 (FIG. 4C). Similar effects were seen in podocytes. Control cells are treated with vehicle alone; all other columns represent cells treated with interferon beta alone or with inhibitor at the indicated concentration.
Figure 4B:
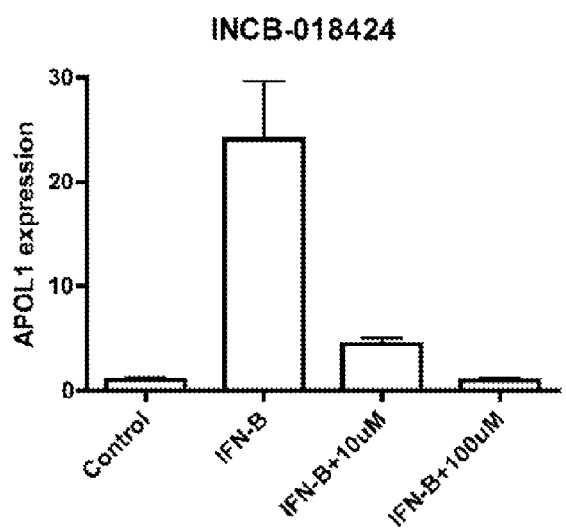
Figure 4C:
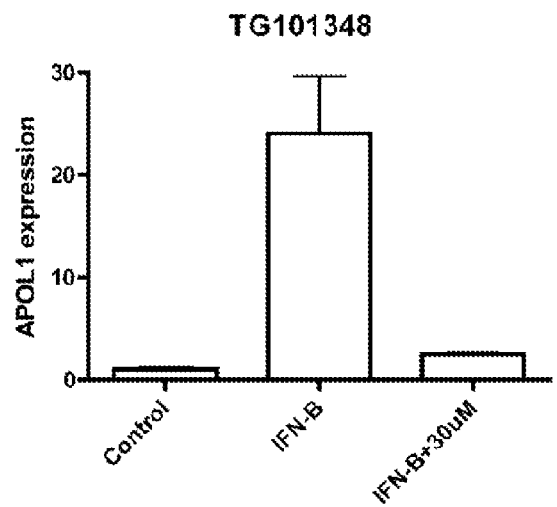

JAK inhibitors are in clinical testing for autoimmune disease, transplant immunosuppression, and myelodysplastic syndromes. They are selective, rather than specific, for individual JAK inhibitors. For example, WHI-P131 targets JAK3, INCB018424 (ruxolitinib) targets JAM and JAK2, and TG101348 targets JAK2. APOL1 mRNA expression was measured in endothelial cells treated with interferon beta and various JAK inhibitors. As shown in FIGS. 4A-4C, the JAK inhibitors block the potentially pathologic upregulation of APOL1 caused by interferon beta treatment. Similar effects were also seen in podocytes.

Example 5: TLR, Rig, and Intracellular DNA Sensors Also Upregulate APOL1

Figure 5A:
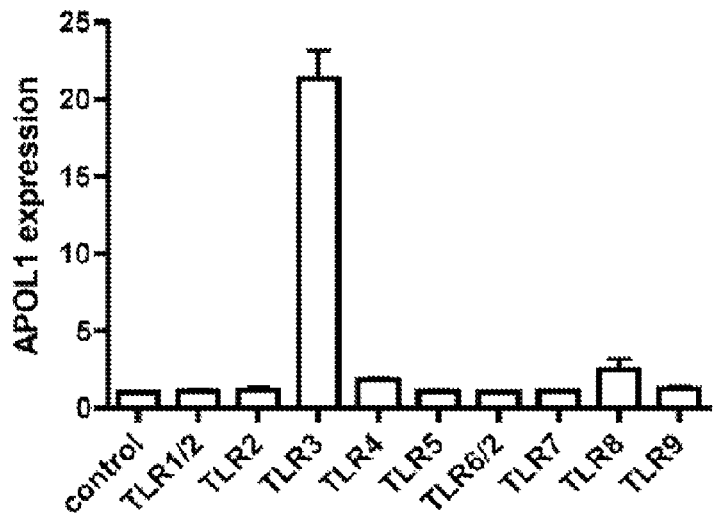
FIGS. 5A and 5B are graphs showing APOL1 expression in endothelials cells (FIG. 5A) and podocytes (FIG. 5B) after treatment with TLR agonists.
Figure 5B:
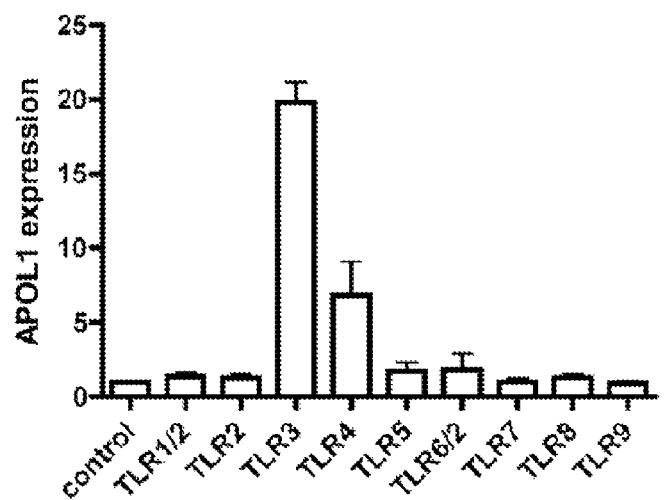
Figure 6A:
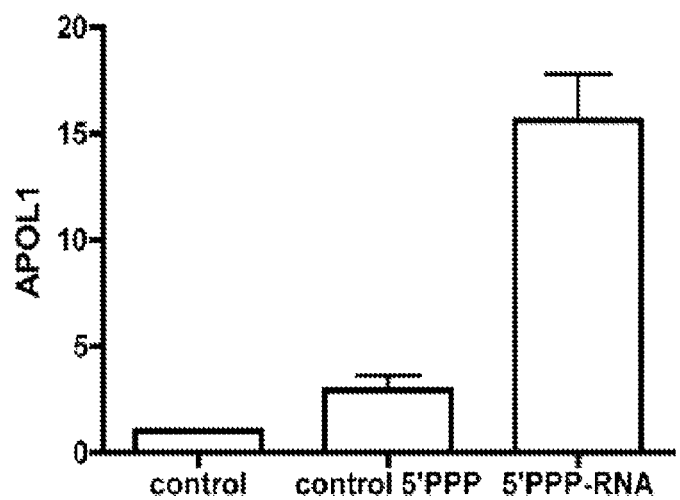
FIGS. 6A and 6B are graphs showing APOL1 expression in endothelial cells (FIG. 6A) and podocytes (FIG. 6B) treated with short, 5' PPP dsRNA, an agonist of cytoplasmic RIG-L1 receptors.
Figure 6B:
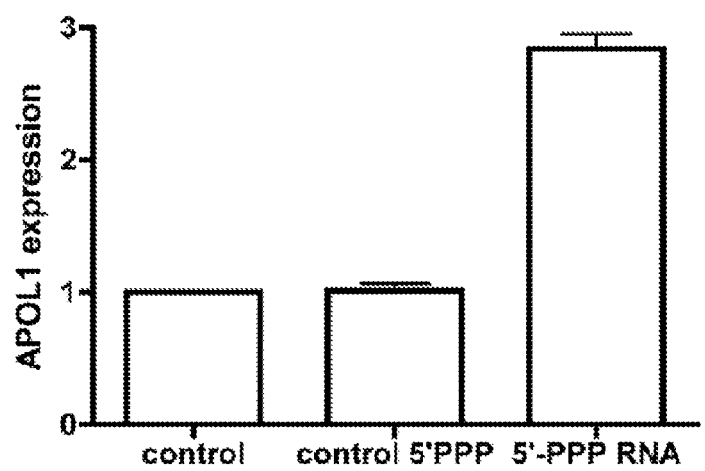
Figure 7:
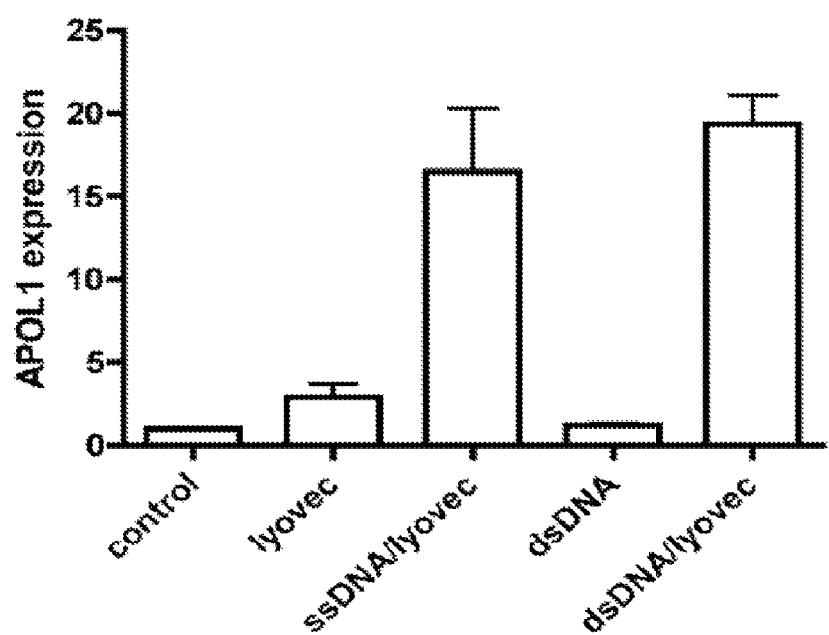
FIG. 7 is a graph showing APOL1 mRNA expression in endothelial cells treated with LPS-free bacterial DNA, with or without the transfection agent Lyovec.
Figure 8A:
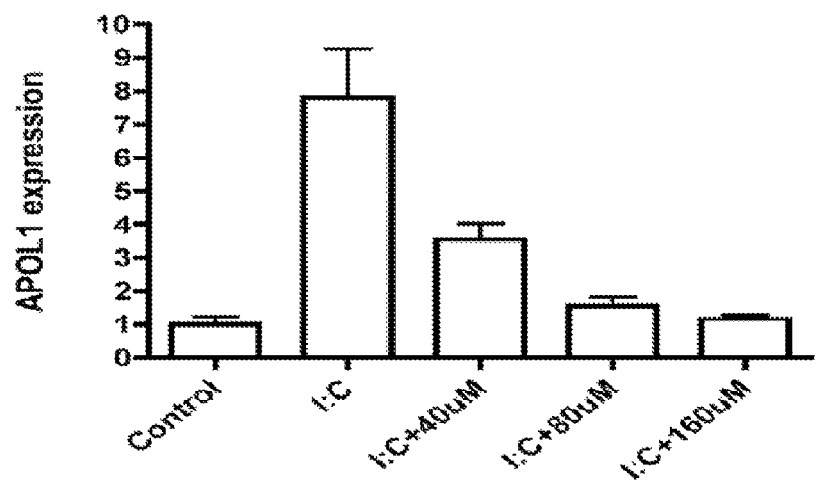
FIGS. 8A, 8B, 8C, and 8D are graphs showing APOL1 mRNA expression in endothelial cells treated with the TLR3 agonist poly(I:C) and different JAK inhibitors: WHI-131 (FIG. 8A), INCB018424 (FIG. 8B), TG101348 (FIG. 8C), CP-690550 (FIG. 8D). Similar effects were seen in podocytes.
Figure 8B:
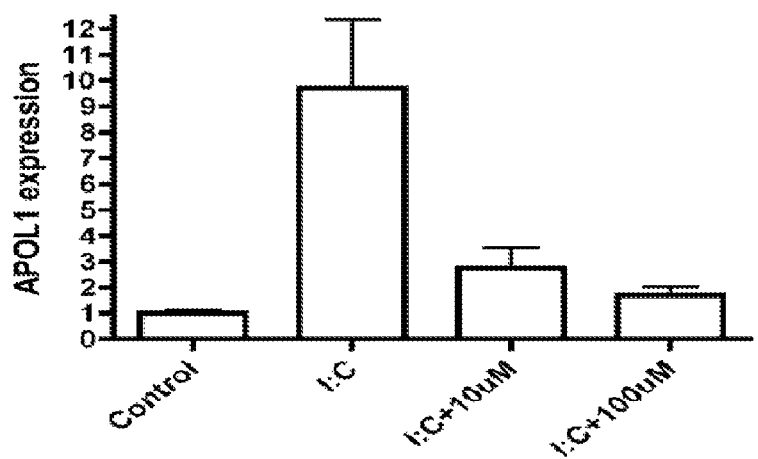
Figure 8C:
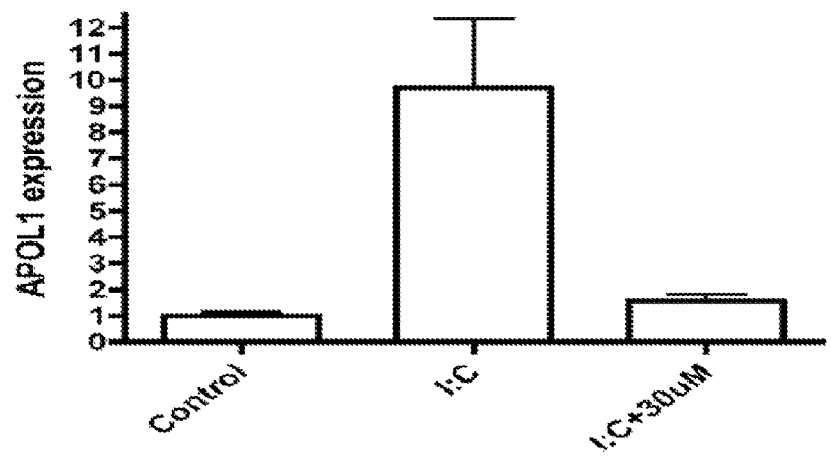
Figure 8D:
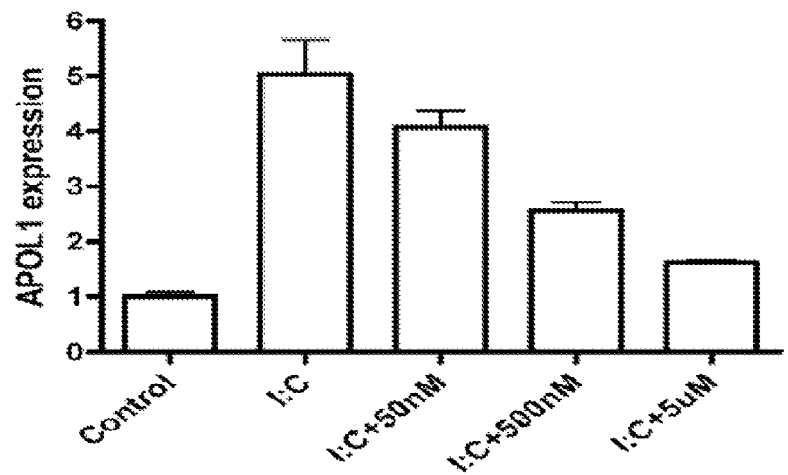

HIV is a powerful inducer of APOL1 renal disease in individuals with the renal risk genotype. Other viruses such as parvovirus have been associated with FSGS. Viral sensing stimulates APOL1 expression. Cells have extracellular, endosomal, and cytoplasmic viral sensors such as TLRs, Rig-L1, and others. These genes are potential targets for reducing APOL1 expression. FIGS. 5A-5B show large increases in APOL1 expression in endothelial cells (FIG. 5A) and podocytes (FIG. 5B) after treatment with TLR agonists. FIGS. 6A-6B show increases in APOL1 expression in endothelial cells (FIG. 6A) and podocytes 9 FIG. 6B) treat with short, 5' PPP dsRNA, an agonist of cytoplasmic RIG-L1 receptors. FIG. 7 shows an increase in APOL1 mRNA expression in endothelial cells treated with LPS-free bacterial DNA, with or without the transfection agent Lyovec.

Figure 9:
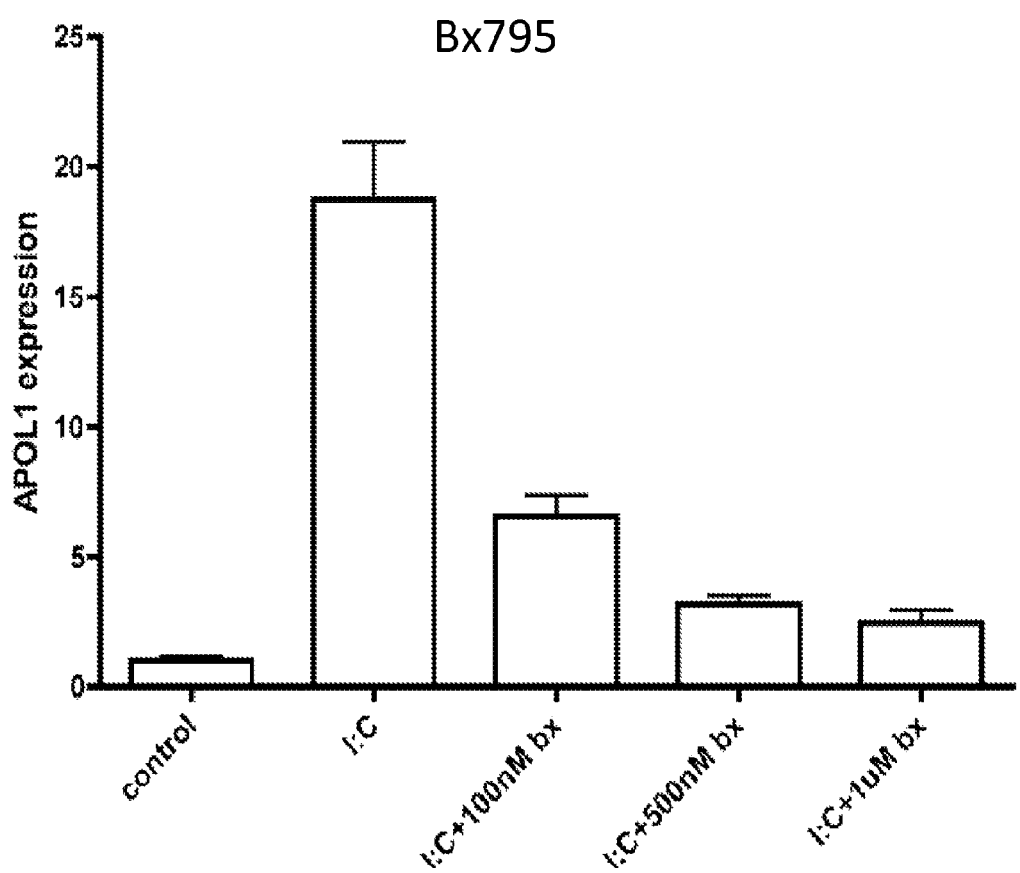
FIG. 9 is a graph showing APOL1 expression levels in endothelial cells treated with TLR3 agonist poly(I:C) and the TBK1/IKKe inhibitor Bx795. Similar results were obtained in podocytes. This kinase complex is used by both TLR and Rig-like receptor signaling mechanisms, and therefore offers a broader target for inhibition of APOL1 expression than either pathway alone.
Figure 10:
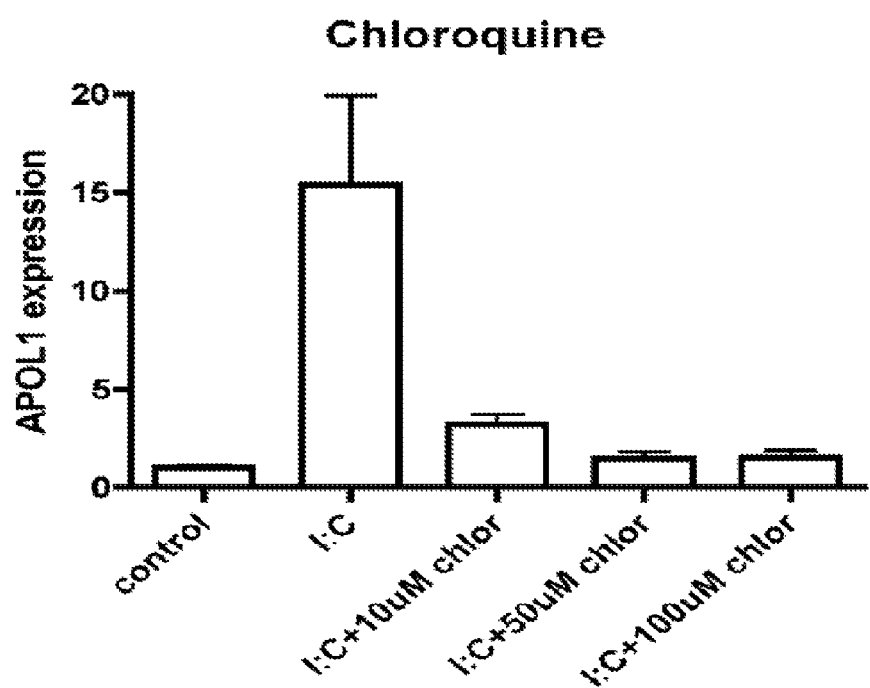
FIG. 10 is a graph showing APOL1 expression levels in endothelial cells treated with TLR3 agonist poly(I:C) and the endosomal acidification inhibitor chloroquine. Similar results were obtained in podocytes. This class of compounds may be particularly useful for inhibiting APOL1 expression when that expression is driven by endosomal pattern recognition receptors such as TLR3, TLR7, TLR8, TLR9, and in some cases TLR4.

Example 6: JAK Inhibitors, Bx795 (a TBK1/IKKe Inhibitor), and Chloroquine Block the TLR3-Stimulated APOL1 Upregulation Endothelial cells were treated with the TLR3 agonist poly(I:C) and with JAK inhibitors (FIGS. 8A-8D), Bx795(a TBK1/IKKe inhibitor) (FIG. 9), and chloroquine (FIG. 10). The JAK inhibitors reduced the poly(I:C) induced increased in APOL1 expression, as did Bx795, and chloroquine. These results demonstrate that blocking diverse pathways may be a strategy to reduce pathogenic APOL1 expression and provides not only treatment options in patients with an APOL1 risk allele, but also a multitude of targets for new drug development. The TBK1/IKK e complex is used by both TLR and Rig-like receptor signaling mechanisms, and therefore offers a broader target for inhibition of APOL1 expression than either pathway alone. Chloroquine and similar class of compounds may be particularly useful for inhibiting APOL1 expression when that expression is driven by endosomal pattern recognition receptors such as TLR3, TLR7, TLR8, TLR9, and in some cases TLR4. Even though TLR3 expression is described above as an example, these strategies are likely to be effective in blocking APOL1 expression driven by multiple inflammatory stimuli.

Figure 11:
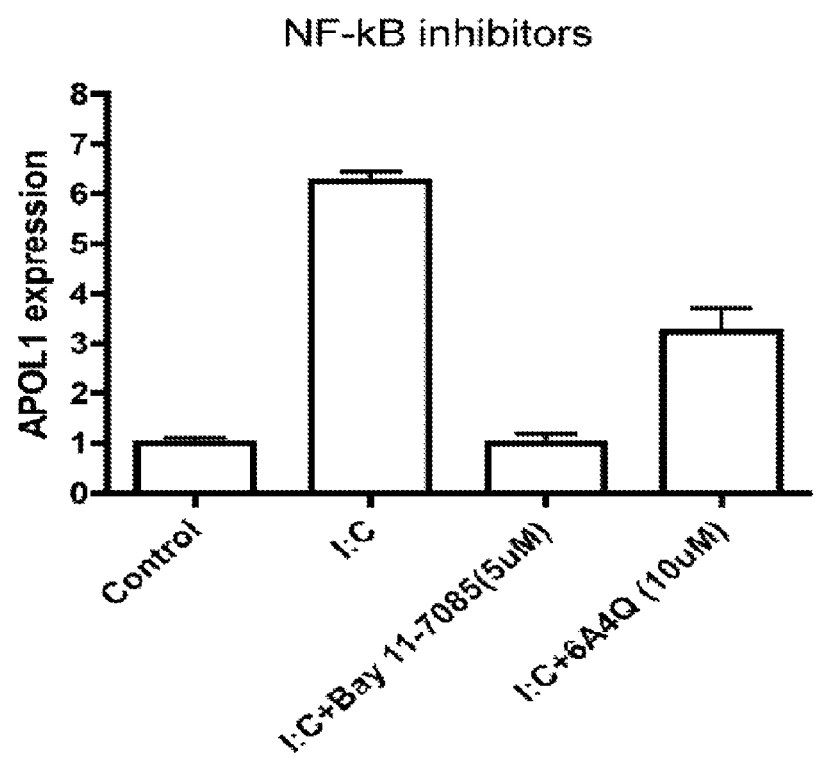
FIG. 11 is a graph showing APOL1 expression stimulated by polyI:C was inhibited by 2 different NF-kB inhibitors. The first inhibitor, Bay 11-7085, blocks phosphorylation of IκB, thereby preventing translocation of NF-kB subunits to the nucleus where they regulate gene expression (in this case APOL1). The second, 6-amino-4-(4-phenoxyphenylethylamino) quinazoline (abbreviated 6A4Q), inhibits NF-kB transcriptional activation of target genes. Inhibition at two different steps of the NF-kB activation of APOL1 expression suggests that any of several hundred other known inhibitors of NF-kB signaling may be useful in suppressing APOL1 expression.
Figure 12:
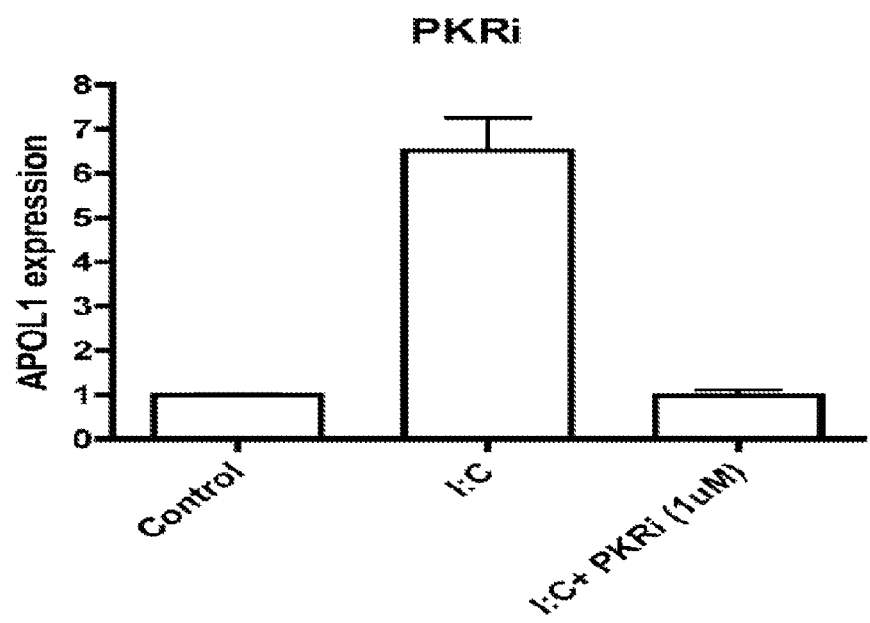
FIG. 12 is a graph showing that an imidazolo-oxindole PKR inhibitor (chemical formula $C_{13}H_8N_4OS$—EMD chemicals) blocks APOL1 upregulation.
Figure 13:
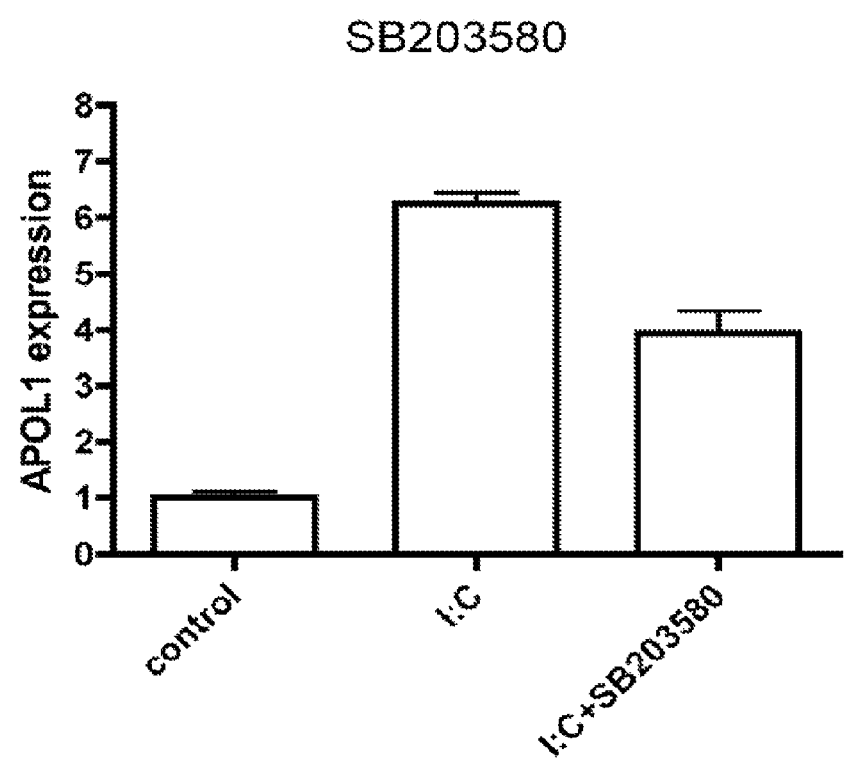
FIG. 13 is a graph showing that a MAP kinase (p38) inhibitor SB203580 inhibited APOL1 expression in endothelial cells, consistent with existing chromatin immunoprecipitation data showing AP-1 binding sites in the APOL1 promoter.

Example 7: NF-κB Inhibitors, PKR Inhibitors, and MAP Kinase Inhibitors all Block Increased APOL1 Expression Driven by Inflammatory Stimuli Induced by a TLR3 Agonist Endothelial cells were treated with the TLR3 agonist poly(I:C) and with NF-κB inhibitors (FIG. 11), PKR inhibitors (FIG. 12), and MAP kinase inhibitors (FIG. 13).

APOL1 expression stimulated by poly(I:C) could be inhibited by 2 different NF-kB inhibitors. The first inhibitor, Bay 11-7085, blocks phosphorylation of IkBa, thereby preventing translocation of NF-kB subunits to the nucleus where they regulate gene expression (in this case APOL1). The second, 6-amino-4-(4-phenoxyphenylethylamino) quinazoline (abbreviated 6A4Q), inhibits NF-kB transcriptional activation of target genes. Inhibition at two different steps of the NF-kB activation of APOL1 expression suggests that any of several hundred other known inhibitors of NF-kB signaling may be useful in suppressing blocked poly(I:C) induced APOL1 upregulation.

To block the PKR pathway, an imidazolo-oxindole PKR inhibitor (chemical formula $C_{13}H_8N_4OS$-EMD chemicals) was used. This inhibitor has the structure

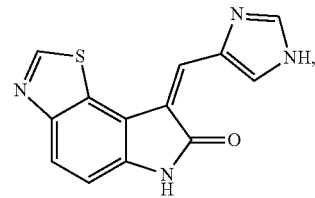 [SMILES: O=C1Nc2ccc3ncsc3c2/C1=C/c1c[nH]cn1]

and completely blocked poly(I:C) induced APOL1 upregulation.

The MAP kinase (p38) inhibitor SB203580 also inhibited blocked poly(I:C) induced APOL1 upregulation in endothelial cells, consistent with existing chromatin immunoprecipitation data showing AP-1 binding sites in the APOL1 promoter. In podocytes, the JNK inhibitor SP600125 inhibited APOL1 expression by 50% (not shown).

Example 8: shRNA Knockdown Experiments

To validate pharmacologic targets that may regulate pathogenic APOL1 expression, we used shRNA to determine specific genes that mediate the APOL1 upregulation induced by poly(I:C). These experiments allowed us to confirm targets identified above by pharmacologic methods and to identify additional known targets in these same pathways. Reduced APOL1 expression (which was induced by poly(I:C) stimulus) was seen with knockdown of JAKs, STATs, IRFs, NF-κB pathway genes (NEMO, REL-A), and genes involved in TLR signaling (TLR3, Ticam, TBK1).

Figure 14:
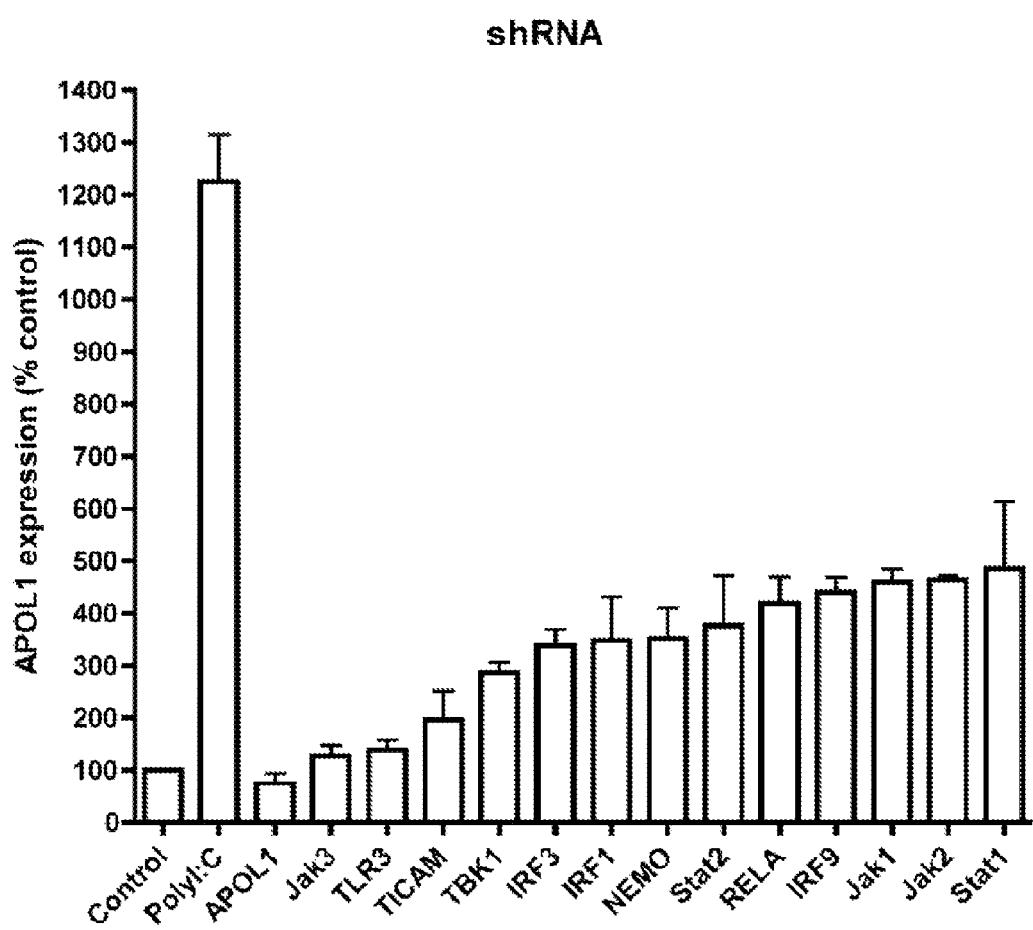
FIG. 14 is a graph showing that the TLR3 agonist polyI:C strongly stimulates APOL1 expression. Lanes 1 is the control, and lane 2 is poly(I:C) treated. Virus expressing green fluorescent protein was used as the viral control in both lanes 1 and 2. All other lanes received polyI:C plus virally delivered shRNA for the specified gene. Reduced APOL1 expression is seen with knockdown of Jak kinases, Stats, IRFs, NF-kB pathway genes (NEMO, REL-A), and genes involved in TLR signaling (TLR3, Ticam, TBK1).

The data shown in FIG. 14 validates several pathways identified by the pharmacological experiments described above and identifies additional pathways that can be targeted to decrease pathogenic APOL1 expression.

OTHER EMBODIMENTS

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described herein. The term "comprises" means "includes." In case of conflict, the present specification, including explanations of terms, will control.

In addition, the materials, methods, and examples are illustrative only and not intended to be limiting.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All publications and patent applications mentioned in this specification are herein incorporated by reference to the same extent as if each independent publication or patent application was specifically and individually indicated to be incorporated by reference in their entirety.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

The invention claimed is:

1. A method of treating or reducing the likelihood of developing a renal nephropathy in a subject having been identified as having an APOL1 genotype selected from the group consisting of:
    (i) two copies of the G1 allele of APOL1;
    (ii) two copies of the G2 allele of APOL1; or
    (iii) one copy of the G1 allele of APOL1 and one copy of the G2 allele of APOL1,
    wherein the method comprises administering to the subject an antagonist of the tumor necrosis factor (TNF) receptor-associated factor NF-kB activator (TANK) binding kinase 1 (TBK1)/I κB kinase e (IKKe) pathway.

2. The method of claim 1, wherein said antagonist of the TBK1/IKKe pathway is selected from the group consisting of auranofinc, PS-1145 dihydrochloride, wedelolactone, IKK inhibitor X, butein, IKK16, and Bx795.

3. The method of claim 1, wherein said renal nephropathy damages the kidneys.

4. The method of claim 1, wherein said subject has one copy of the G1 allele and one copy of the G2 allele.

5. The method of claim 1, wherein said subject is of African or Hispanic ancestry.

6. The method of claim 5, wherein said subject is an African-American subject.

7. The method of claim 1, further comprising administering to said subject a therapeutic agent.

8. The method of claim 7, wherein said therapeutic agent is a blood pressure medication, a steroid, or an immunosuppressive agent.

9. The method of claim 8, wherein
    i) said blood pressure medication is a diuretic, wherein preferably said diuretic is selected from chlorthalidone, chlorothiazide, furosemide, hydrochlorothiazide, indapamide, metolazone, amiloride hydrochloride, spironolactone, triamterene, bumetanide, and combinations thereof; an alpha adrenergic antagonist, wherein preferably said alpha adrenergic antagonist is selected from alfuzosin, doxazosin, prazosin, terazosin, or tamsulosin, and combinations thereof; a central adrenergic inhibitor, wherein preferably said central adrenergic inhibitor is selected from clonidine, guanfacine, methyldopa, and combinations thereof; an angiotensin converting enzyme (ACE) inhibitor, whrein said ACE inhibitor is selected from benazepril, captopril, enalapril, fosinopril, lisinopril, moexipril, perindopril, quinapril, ramipril, trandolapril, and combinations thereof; an angiotensin II receptor blocker, wherein said angiotensin II receptor blocker is selected from candesartan, eprosartan, irbesartan, losartan, olmesartan, telmisartan, valsartan, and combinations thereof; an alpha blocker, wherein said alpha blocker is selected from doxazosin, prazosin, terazosin, and combinations thereof; a beta blocker, wherein said beta blocker is selected from acebutolol, atenolol, betaxolol, bisoprolol, carteolol, metoprolol, nadolol, nebivolol, penbutolol, pindolol, propranolol, solotol, timolol, and combinations thereof; a calcium channel blocker, wherein said calcium channel blocker is selected from amlodipine, bepridil, diltiazem, felodipine, isradipine, nicardipine, nifedipine, nisoldipine, verapamil, and combinations thereof); a vasodilator, wherein said vasodilator is selected from hydralazine, minoxidil, and combinations thereof; and a renin inhibitor, such as aliskiren, and combinations thereof; and/or
    i) said steroid is selected from a corticosteroid, such as cortisone, prednisone, methylprednisolone, prednisolone, and combinations thereof; an anabolic steroid, such as anatrofin, anaxvar, annadrol, bolasterone, decadiabolin, decadurabolin, dehydroepiandrosterone (DHEA), delatestryl, dianabol, dihydrolone, durabolin, dymethazine, enoltestovis, equipoise, gamma hydroxybutyrate, maxibolin, methanedriol, methyltestosterone, parabolin, primobolin, quinolone, therabolin, trophobolene, winstrol, and combinations thereof; and/or
    ii) said immunosuppressive agent is a glucocorticoid, a cytostatic, an antibody, or an anti-immunophilin and/or mychophenolate mofetil (MMF), FK-506, azathioprine, cyclophosphamide, methotrexate, dactinomycin, antithymocyte globulin (ATGAM), an anti-CD20-antibody, a muromonoab-CD3 antibody, basiliximab, daclizumab, cyclosporin, tacrolimus, voclosporin, sirolimus, an interferon, infliximab, etanercept, adalimumab, fingolimod, myriocin, and combinations thereof.

10. The method of claim 1, wherein the subject has not had a kidney transplant prior to administration of the antagonist.

11. The method of claim 3, wherein said renal nephropathy is selected from the group consisting of focal segmental glomerulosclerosis (FSGS), end-stage kidney disease (ESKD), hypertensive ESKD, nephropathy secondary to systemic lupus erythematosus, diabetic nephropathy, hypertensive nephropathy, IgA nephropathy, nephritis, human immunodeficiency virus (HIV)-associated nephropathy, and xanthine oxidase deficiency.

12. The method of claim 1, wherein said subject has two copies of the G1 allele.

13. The method of claim 1, wherein said subject has two copies of the G2 allele.

* * * * *

UNITED STATES PATENT AND TRADEMARK OFFICE
CERTIFICATE OF CORRECTION

PATENT NO. : 10,940,151 B2
APPLICATION NO. : 16/179100
DATED : March 9, 2021
INVENTOR(S) : David J. Friedman et al.

It is certified that error appears in the above-identified patent and that said Letters Patent is hereby corrected as shown below:

In the Claims

Column 37, Claim 1, Line 20, replace "(TBK1)/I κB" with --(TBK1)/ IκB--.
    Claim 2, Line 24, replace "auranofinc" with --auranofin--.
    Claim 9, Line 52, replace "whrein" with --wherein--.

Column 38, Claim 9, Line 15, replace "solotol" with --solutol--.
    Line 24, replace "i) said steroid" with --ii) said steroid--.
    Line 31, replace "methanedriol" with --methandriol--.
    Line 32, replace "primobolin" with --primobolan--.
    Line 34, replace "ii) said immunosuppressive" with --iii) said immunosuppressive--.
    Line 39, replace "muromonoab-CD3" with --muromonab-CD3--.

Signed and Sealed this
Twentieth Day of July, 2021

Drew Hirshfeld
*Performing the Functions and Duties of the
Under Secretary of Commerce for Intellectual Property and
Director of the United States Patent and Trademark Office*